US011952601B2

(12) United States Patent
Hofmann et al.

(10) Patent No.: US 11,952,601 B2
(45) Date of Patent: Apr. 9, 2024

(54) RECOMBINANT BOTULINUM TOXIN WITH INCREASED DURATION OF EFFECT

(71) Applicant: MERZ PHARMA GMBH & CO. KGAA, Frankfurt am Main (DE)

(72) Inventors: Fred Hofmann, Potsdam (DE); Marcel Jurk, Berlin (DE); Manuela López De La Paz, Liederbach am Taunus (DE); Daniel Scheps, Potsdam (DE); Jürgen Frevert, Berlin (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 379 days.

(21) Appl. No.: 16/498,193

(22) PCT Filed: Jun. 20, 2017

(86) PCT No.: PCT/EP2017/065096

§ 371 (c)(1),
(2) Date: Sep. 26, 2019

(87) PCT Pub. No.: WO2018/233813

PCT Pub. Date: Dec. 27, 2018

(65) Prior Publication Data

US 2020/0048624 A1 Feb. 13, 2020

(51) Int. Cl.
*C07K 14/33* (2006.01)
*A61K 8/66* (2006.01)
(Continued)

(52) U.S. Cl.
CPC .................. *C12N 9/52* (2013.01); *A61K 8/66* (2013.01); *C12Y 304/24069* (2013.01); *A61K 38/00* (2013.01); *C07K 2319/31* (2013.01)

(58) Field of Classification Search
None
See application file for complete search history.

(56) References Cited

U.S. PATENT DOCUMENTS 6,903,187 B1 6/2005 Steward et al.
7,491,799 B2 2/2009 Steward et al.
(Continued)

FOREIGN PATENT DOCUMENTS

EP 2369005 9/2011
EP 3335719 6/2018
(Continued)

OTHER PUBLICATIONS

Kukreja et al. (2015) "The botulinum toxin as a therapeutic agent: molecular and pharmacological insights," Research and Reports in Biochemistry 5: 173-183.

(Continued)

*Primary Examiner* — Marsha Tsay
(74) *Attorney, Agent, or Firm* — Leydig, Voit & Mayer, Ltd.

(57) ABSTRACT

This invention relates to novel recombinant clostridial neurotoxins exhibiting an increased duration of effect without a delayed onset of effect and to methods for the manufacture of such recombinant clostridial neurotoxins. These novel recombinant clostridial neurotoxins comprise a domain consisting of proline, alanine, serine, threonine, glycine and glutamate residues, and the methods comprise the steps of inserting a nucleic acid sequence coding for said domain into a nucleic acid sequence coding for a parental clostridial neurotoxin and expression of the recombinant nucleic acid sequence comprising said domain-coding sequence in a host cell. The invention further relates to novel recombinant single-chain precursor clostridial neurotoxins used in such methods, nucleic acid sequences encoding such recombinant single-chain precursor clostridial neurotoxins, and pharmaceutical compositions comprising the recombinant
(Continued)

Figure 1:

clostridial neurotoxin with an increased duration of effect without a delayed onset of effect.

16 Claims, 3 Drawing Sheets

Specification includes a Sequence Listing.

(51) Int. Cl.

| | |
|---|---|
| ***A61K 38/16*** | (2006.01) |
| ***C12N 9/52*** | (2006.01) |
| ***C12N 15/52*** | (2006.01) |
| ***C12N 15/70*** | (2006.01) |
| *A61K 38/00* | (2006.01) |

(56) References Cited

U.S. PATENT DOCUMENTS

| | | | |
|---|---|---|---|
| 8,444,991 | B2 | 5/2013 | Randolph et al. |
| 8,563,521 | B2 | 10/2013 | Skerra et al. |
| 8,748,151 | B2 | 6/2014 | Frevert |
| 8,808,710 | B2 | 8/2014 | Randolph et al. |
| 9,050,246 | B2 | 6/2015 | Bertholon et al. |
| 9,050,336 | B2 | 6/2015 | Blanda et al. |
| 9,260,494 | B2 | 2/2016 | Skerra et al. |
| 9,388,394 | B2 | 7/2016 | Heinrichs et al. |
| 9,758,573 | B2 | 9/2017 | Vartanian et al. |
| 9,809,809 | B2 | 11/2017 | Schmidt et al. |
| 9,827,298 | B2 | 11/2017 | Hofmann et al. |
| 9,975,929 | B2 | 5/2018 | Frevert et al. |
| 10,022,424 | B2 | 7/2018 | Stossel et al. |
| 2002/0127247 | A1 | 9/2002 | Steward et al. |
| 2009/0155314 | A1 | 6/2009 | Tezel et al. |
| 2010/0172940 | A1 | 7/2010 | Petrella |
| 2012/0135937 | A1 | 5/2012 | Bertholon et al. |
| 2012/0141532 | A1 | 6/2012 | Blanda et al. |
| 2012/0295914 | A1 | 11/2012 | Villard et al. |
| 2013/0165389 | A1 | 6/2013 | Schellenberger et al. |
| 2015/0044250 | A1 | 2/2015 | Heinrichs et al. |
| 2015/0320743 | A1 | 11/2015 | Bertholon et al. |
| 2015/0322118 | A1 | 11/2015 | Groer et al. |
| 2017/0058006 | A1 | 3/2017 | Frevert et al. |
| 2018/0141982 | A1 | 5/2018 | Anderson et al. |
| 2018/0169182 | A1 | 6/2018 | Frevert et al. |
| 2018/0327730 | A1 | 11/2018 | Hofmann et al. |
| 2019/0060422 | A1 | 2/2019 | Fink et al. |
| 2020/0129587 | A1 | 4/2020 | Frevert et al. |
| 2020/0131494 | A1 | 4/2020 | Frevert et al. |
| 2020/0354706 | A1 | 11/2020 | Frevert et al. |
| 2021/0008156 | A1 | 1/2021 | Frevert et al. |

FOREIGN PATENT DOCUMENTS

| | | |
|---|---|---|
| EP | 3649143 | 5/2020 |
| RU | 2530604 | 7/2013 |
| WO | WO 1995/032738 | 12/1995 |
| WO | WO 1996/039166 | 12/1996 |
| WO | WO 2000/012728 | 3/2000 |
| WO | WO 2001/014570 | 3/2001 |
| WO | WO 2002/008268 | 1/2002 |
| WO | WO 2002/040506 | 5/2002 |
| WO | WO 2005/007185 | 1/2005 |
| WO | WO 2005/068494 | 7/2005 |
| WO | WO 2006/017749 | 2/2006 |
| WO | WO 2006/020208 | 2/2006 |
| WO | WO 2006/076902 | 7/2006 |
| WO | WO 2008/155134 | 12/2008 |
| WO | WO 2009/114748 | 9/2009 |
| WO | WO 2010/028025 | 3/2010 |
| WO | WO 2010/091122 | 8/2010 |
| WO | WO 2010/136585 | 12/2010 |
| WO | WO 2010/136594 | 12/2010 |
| WO | WO 2011/109130 | 9/2011 |
| WO | WO 2011/123813 | 10/2011 |
| WO | WO 2011/144756 | 11/2011 |
| WO | WO 2012/052562 | 4/2012 |
| WO | WO 2013/049508 | 4/2013 |
| WO | WO 2013/068472 | 5/2013 |
| WO | WO 2013/068476 | 5/2013 |
| WO | WO 2013/082116 | 6/2013 |
| WO | WO 2013/112867 | 8/2013 |
| WO | WO 2014/068317 | 5/2014 |
| WO | WO 2014/086494 | 6/2014 |
| WO | WO 2014/207109 | 12/2014 |
| WO | WO 2015/132004 | 9/2015 |
| WO | WO 2015/183044 | 12/2015 |
| WO | WO 2016/025626 | 2/2016 |
| WO | WO 2016/073562 | 5/2016 |
| WO | WO 2016/110662 | 7/2016 |
| WO | WO 2016/180533 | 11/2016 |
| WO | WO 2016/198163 | 12/2016 |
| WO | WO 2017/125487 | 7/2017 |
| WO | WO 2018/233813 | 12/2018 |
| WO | WO 2019/007509 | 1/2019 |
| WO | WO 2019/081022 | 5/2019 |
| WO | WO 2019/101308 | 5/2019 |
| WO | WO 2020/088667 | 5/2020 |

OTHER PUBLICATIONS

Owen et al. (May 2017) "Hyaluronic Acid," Comprehensive Biomaterials II, Chapter 2.14 2: 306-331, Abstract Only (3 pages).

Tosoh Application Note (2020) "Analysis of Hyaluronic Acid Using the EcoSEC® GPC System," Available online at https://www.ecosec.eu//SharedTBGFilelibrary/TBG/Products%20Download/Application%20Note/a17i17a.pdf, pp. 1-3.

USPTO Office Action, dated Mar. 2, 2021, corresponding to U.S. Appl. No. 16/079,367, 11 pp.

U.S. Appl. No. 16/498,257, filed Sep. 26, 2019, Pending.

U.S. Appl. No. 16/755,848, filed Apr. 13, 2020, Pending.

U.S. Appl. No. 16/760,377, filed Apr. 29, 2020, Pending.

Aoki (2001) "A comparison of the safety margins of botulinum neurotoxin serotypes A, B, and F in mice," Toxicon 39: 1815-1820.

"Botulinum neurotoxin type E non-toxic component," (1993) available online at https://www.ncbi.nlm.nih.gov/protein/p46082, accessed Dec. 2017.

"BPXTEN construction related XTEN polypeptide sequence SEQ ID 767," XP002776714, retrieved from EBI accession No. GSP: AYG93920, Database accession No. AYG93920 Sep. 2010, 2 pp.

Cox (2008) "Botox Jabs: A New Weapon Against Chronic Pain," ABC News, available online at https://abcnews.go.com/Health/PainManagement/story?id=4148566&page=1, 2 pp.

Fernandez-Salas et al. (2004) "Plasma membrane localization signals in the light chain of botulinum neurotoxin," Proc. Natl. Acad. Sci. U.S.A. 101(9): 3208-3213.

Li et al. (1998) "Molecular characterization of type E Clostridium botulinum and comparison to other types of Clostridium botulinum," Biochim. Biophys. Acta. 1395(1):21-27.

Schlapschy et al. (2013) "PASylation: a biological alternative to PEGylation for extending the plasma half-life of pharmaceutically active proteins," Protein Engineering, Design and Selection 26(8): 489-501.

Search Report dated May 6, 2015, corresponding to International Application No. PCT/EP2015/000489 (filed Mar. 4, 2015), 4 pp.

Search Report and Written Opinion, dated Sep. 26, 2016, corresponding to International Application No. PCT/EP2016/000962 (filed Jun. 10, 2016), 10 pp.

Search Report and Written Opinion, dated Jan. 8, 2018, corresponding to International Application No. PCT/EP2017/065096 (filed Jun. 20, 2017), 10 pp.

Stancombe et al. (Feb. 2012) "Engineering botulinum neurotoxin domains for activation by toxin light chain," Febs Journal 279(3): 515-523.

Wang et al. (2011) "A Dileucine in the Protease of Botulinum Toxin A Underlies Its Long-lived Neuroparalysis," J. Biol. Chem. 286(8): 6375-6385.

U.S. Appl. No. 16/079,367, filed Aug. 23, 2018, Pending.

(56) References Cited

OTHER PUBLICATIONS

Binz et al. (2018) Abstract for "Mutations in Light Chain of Botulinum Neurotoxin A Enable Cleavage of Human SNAP-23," Abstracts/Toxicon 156: p. S10.
European Search Report, dated Aug. 29, 2016, corresponding to European Patent Application No. 16 15 8302.6, 5 pp.
Fan et al. (2015) "Monoclonal Antibodies Targeting the Alpha-Exosite of Botulinum Neurotoxin Serotype/A Inhibit Catalytic Activity," PLoS ONE 10(8): 1-23.
Ganceviciene et al. (2012) "Skin anti-aging strategies," Dermato-endocrinology 4(3): 308-319.
International Search Report and Written Opinion in corresponding International Patent Application No. PCT/EP2017/054596, dated May 23, 2017, 9 pp.
International Preliminary Report on Patentability in corresponding International Patent Application No. PCT/EP2017/054596, dated Sep. 4, 2018, 7 pp.
Kolbin et al. (2014) "Pharmacoepidemiology of botulinum toxin preparations in comprehensive post-stroke spasticity therapy in the Russian Federation: Survey data from neurologists" Kachestvennaya Klinicheskaya Praktika 3: 13 pages.
Kumaran et al. (2008) "Substrate Binding Mode and Its implication on Drug Design for Botulinum Neurotoxin A," PLoS Pathogens 4(9): e1000165, pp. 1-9.
Pearson et al. (1988) "Improved tools for biological sequence comparison," PNAS 85(8):2444-2448.
Shao et al. (Nov. 2019) "Construction of functional chimeras of syntaxin-1A and its yeast orthologue, and their application to the yeast cell-based assay for botulinum neurotoxin serotype C," BBA-General Subjects 1863: 129396, pp. 1-12.
USPTO Office Action, dated Dec. 10, 2020, corresponding to U.S. Appl. No. 16/498,257, 22 pp.
Wang et al. (2013) "Comparison of the catalytic properties of the botulinum neurotoxin subtypes A1 and A5," Biochimica et Biophysica Acta 1843: 2722-2728.
Altschul et al. (1990) "Basic local alignment search tool," J. Mol. Bio. 215(3): 403-410.
Arndt et al. (2006) "A Structural Perspective of the Sequence Variability Within Botulinum Neurotoxin Subtypes A1-A4," Journal of Molecular Biology 362(4): 733-742.
Band et al. (2010) "Recombinant derivatives of botulinum neurotoxin A engineered for trafficking studies and neuronal delivery," Protein Expression and Purification, Academic Press 71(1): 62-73.
Breidenbach et al. (2004) "Substrate recognition strategy for botulinum neurotoxin serotype A," Nature 432: 925-929.
Dressler et al. (2005) "Mouse diaphragm assay for detection of antibodies against botulinum toxin type B," Movement Disorders 20(12): 1617-1619.
Hallis et al. (1996) "Development of novel assays for botulinum type A and B neurotoxins based on their endopeptidase activities," J. Clin. Microbiol. 34(8): 1934-1938.
Higgins et al. (1989) "Fast and sensitive multiple sequence alignments on a microcomputer," CABIOS 5(2): 151-153.
International Preliminary Report on Patentability, dated Jan. 2, 2020, corresponding to International Application No. PCT/EP2017/065096 (filed Jun. 20, 2017), 7 pp.
International Preliminary Report on Patentability, dated Jan. 16, 2020, corresponding to International Application No. PCT/EP2017/066891 (filed Jul. 6, 2017), 9 pp.
International Preliminary Report on Patentability, dated May 7, 2020, corresponding to International Application No. PCT/EP2017/077427 (filed Oct. 28, 2017), 8 pp.
International Preliminary Report on Patentability, dated Jun. 4, 2020, corresponding to International Application No. PCT/EP2017/080117 (filed Nov. 22, 2017), 11 pp.
Jones et al. (2008) "Development of improved SNAP25 endopeptidase immunoassays for botulinum type A and E toxins," J. of Immunological Methods 329(1-2): 92-101.
Keller (2006) "Recovery from botulinum neurotoxin poisoning in vivo," Neuroscience 139(2): 629-637.
Needleman et al. (1970) "A general method applicable to the search for similarities in the amino acid sequence of two proteins," J Mol Biol 48: 443-453.
Pearce et al. (1994) "Measurement of Botulinum Toxin Activity: Evaluation of the Lethality Assay," Toxicol. Appl. Pharmacol. 128(1): 69-77.
Ravichandran et al. (2006) "An Initial Assessment of the Systemic Pharmacokinetics of Botulinum Toxin," JPET 318(3):1343-1351.
Search Report and Written Opinion, dated Dec. 1, 2017, corresponding to International Application No. PCT/EP2017/066891 (filed Jul. 6, 2017), 12 pp.
Search Report and Written Opinion, dated Feb. 20, 2018, corresponding to International Application No. PCT/EP2017/077427 (filed Oct. 26, 2017), 11 pp.
Search Report and Written Opinion, dated Jun. 18, 2018, corresponding to International Application No. PCT/EP2017/080117 (filed Nov. 22, 2017), 18 pp.
Smith et al. (1981) "Comparison of biosequences," Adv Appl Math 2: 482-489.
USPTO Office Action, dated Jun. 29, 2020, corresponding to U.S. Appl. No. 16/498,257, 9 pp.
Vazquez-Cintron et al. (Aug. 2016) "Pre-Clinical Study of a Novel Recombinant Botulinum Neurotoxin Derivative Engineered for Improved Safety," Scientific Reports 6(1), 30429: 1-10.
Weber (2013) "Inhibierung von Stat5 in Tumoren durch RNA-Interferenz und spezifische Interaktion eines Peptidaptamer-Konstruktes milder DNA-Bindedomane," PhD thesis, Johann-Wolfgang-Goethe Universitat, Frankfurt am Main (Germany).
Xue et al. (2014) "Probing BoNT/A Protease Exosites: Implications for Inhibitor Design and Light Chain Longevity," Biochemistry 53(43): 6820-6824.
Pellet et al. (2018), "*The Light Chain Defines the Duration of Action of Botulinum Toxin Serotype A Subtypes*," mBio; 9(2):e00089-18.
Gupta et al. (2019) "*Hyaluronic Acid: Molecular Mechanisms and Therapeutic Trajectory*," Frontiers in Veterinary Science, vol. 6, Article 192.

Figure 1:
His6
PASTGE
LC
HC
PASTGE
Strep
Thrombin
Thrombin
Thrombin

RECOMBINANT BOTULINUM TOXIN WITH INCREASED DURATION OF EFFECT

CROSS-REFERENCE TO RELATED APPLICATIONS

This application is a U.S. National Stage Application filed under 35 U.S.C. § 371 of International Application No. PCT/EP2017/065096, filed Jun. 20, 2017, which is hereby incorporated by reference in its entirety.

FIELD OF THE INVENTION

This invention relates to novel recombinant clostridial neurotoxins exhibiting increased duration of effect without a delayed onset of effect and to methods for the manufacture of such recombinant clostridial neurotoxins. These novel recombinant clostridial neurotoxins comprise at least one domain wherein said domain comprises an amino acid sequence consisting of at least 50 amino acid residues, wherein said domain consists of proline, alanine, serine, threonine, glycine and glutamate residues, and the methods comprise the steps of inserting a nucleic acid sequence coding for said domain into a nucleic acid sequence coding for a parental clostridial neurotoxin and expression of the recombinant nucleic acid sequence comprising the domain-coding sequence in a host cell. The invention further relates to novel recombinant single-chain precursor clostridial neurotoxins used in such methods, nucleic acid sequences encoding such recombinant single-chain precursor clostridial neurotoxins, and compositions comprising the recombinant clostridial neurotoxin with increased duration of effect without a delayed onset of effect.

BACKGROUND OF THE INVENTION

*Clostridium* is a genus of anaerobe gram-positive bacteria, belonging to the Firmicutes. *Clostridium* consists of around 100 species that include common free-living bacteria as well as important pathogens, such as *Clostridium botulinum* and *Clostridium tetani*. Both species produce neurotoxins, botulinum toxin and tetanus toxin, respectively. These neurotoxins are potent inhibitors of calcium-dependent neurotransmitter secretion of neuronal cells and are among the strongest toxins known to man. The lethal dose in humans lies between 0.1 ng and 1 ng per kilogram of body weight.

Oral ingestion of botulinum toxin via contaminated food or generation of botulinum toxin in wounds can cause botulism, which is characterised by paralysis of various muscles. Paralysis of the breathing muscles can cause death of the affected individual.

Although both botulinum neurotoxin (BoNT) and tetanus neurotoxin (TxNT) function via a similar initial physiological mechanism of action, inhibiting neurotransmitter release from the axon of the affected neuron into the synapse, they differ in their clinical response. While the botulinum toxin acts at the neuromuscular junction and other cholinergic synapses in the peripheral nervous system, inhibiting the release of the neurotransmitter acetylcholine and thereby causing flaccid paralysis, the tetanus toxin acts mainly in the central nervous system, preventing the release of the inhibitory neurotransmitters GABA (gamma-aminobutyric acid) and glycine by degrading the protein synaptobrevin. The consequent overactivity in the muscles results in generalized contractions of the agonist and antagonist musculature, termed a tetanic spasm (rigid paralysis).

While the tetanus neurotoxin exists in one immunologically distinct type, the botulinum neurotoxins are known to occur in seven different immunogenic types, termed BoNT/A through BoNT/G. Most *Clostridium botulinum* strains produce one type of neurotoxin, but strains producing multiple toxins have also been described.

Botulinum and tetanus neurotoxins have highly homologous amino acid sequences and show a similar domain structure. Their biologically active form comprises two peptide chains, a light chain of about 50 kDa and a heavy chain of about 100 kDa, linked by a disulfide bond. A linker or loop region, whose length varies among different clostridial toxins, is located between the two cysteine residues forming the disulfide bond. This loop region is proteolytically cleaved by an unknown clostridial endoprotease to obtain the biologically active toxin.

The molecular mechanism of intoxication by TeNT and BoNT appears to be similar as well: entry into the target neuron is mediated by binding of the C-terminal part of the heavy chain to a specific cell surface receptor; the toxin is then taken up by receptor-mediated endocytosis. The low pH in the so formed endosome then triggers a conformational change in the clostridial toxin which allows it to embed itself in the endosomal membrane and to translocate through the endosomal membrane into the cytoplasm, where the disulfide bond joining the heavy and the light chain is reduced. The light chain can then selectively cleave one or two of the so called SNARE-proteins, which are essential for different steps of neurotransmitter release into the synaptic cleft, e.g. recognition, docking and fusion of neurotransmitter-containing vesicles with the plasma membrane. TeNT, BoNT/B, BoNT/D, BoNT/F, and BoNT/G cause proteolytic cleavage of synaptobrevin or VAMP (vesicle-associated membrane protein), BoNT/A and BoNT/E cleave the plasma membrane-associated protein SNAP-25, and BoNT/C cleaves the integral plasma membrane protein syntaxin and SNAP-25.

Clostridial neurotoxins display variable durations of action that are serotype specific. The clinical therapeutic effect of BoNT/A lasts approximately 3 months for neuromuscular disorders and 6 to 12 months for hyperhidrosis. The effect of BoNT/E, on the other hand, lasts less than 4 weeks. The longer lasting therapeutic effect of BoNT/A makes it preferable for certain clinical use compared to the other serotypes, for example serotypes B, $C_1$, D, E, F, G. One possible explanation for the divergent durations of action might be the distinct subcellular localizations of BoNT serotypes. The protease domain of BoNT/A light chain localizes in a punctate manner to the plasma membrane of neuronal cells, co-localizing with its substrate SNAP-25. In contrast, the short-duration BoNT/E serotype LC is cytoplasmic. Membrane association might protect BoNT/A from cytosolic degradation mechanisms allowing for prolonged persistence of BoNT/A in the neuronal cell.

The onset of the paralytic effect is also different in the neurotoxin serotypes. Whereas the onset of effect of BoNT/E in humans is observed after 0.5-1 day, the onset of the effect of BoNT/A in humans is only after 2-3 days. The peak effect is reached in humans after 1-2 days or 3-7 day after injections of BoNT/E or BoNT/A, respectively. Consequently BoNT/A has a late onset and a long duration of the paralytic effect, in contrast the paralytic effect of BoNT/E starts markedly earlier but lasts markedly less long. The reason for this different onset and different duration of effect is not known.

In *Clostridium botulinum*, the botulinum toxin is formed as a protein complex comprising the neurotoxic component and non-toxic proteins. The accessory proteins embed the neurotoxic component thereby protecting it from degradation by digestive enzymes in the gastrointestinal tract. Thus, botulinum neurotoxins of most serotypes are orally toxic. Complexes with, for example, 450 kDa or with 900 kDa are obtainable from cultures of *Clostridium botulinum.*

In recent years, botulinum neurotoxins have been used as therapeutic agents in the treatment of dystonias and spasms. Preparations comprising botulinum toxin complexes are commercially available, e.g. from Ipsen Ltd (Dysport®) or Allergan Inc. (Botox®). A high purity neurotoxic component, free of any complexing proteins, is for example available from Merz Pharmaceuticals GmbH, Frankfurt (Xeomin®).

Clostridial neurotoxins are usually injected into the affected muscle tissue, bringing the agent close to the neuromuscular end plate, i.e. close to the cellular receptor mediating its uptake into the nerve cell controlling said affected muscle. Various degrees of neurotoxin spread have been observed. The neurotoxin spread is thought to depend on the injected amount and the particular neurotoxin preparation. It can result in adverse side effects such as paralysis in nearby muscle tissue, which can largely be avoided by reducing the injected doses to the therapeutically relevant level. Overdosing can also trigger the immune system to generate neutralizing antibodies that inactivate the neurotoxin preventing it from relieving the involuntary muscle activity. Immunologic tolerance to botulinum toxin has been shown to correlate with cumulative doses and in addition on short injection intervals.

At present, clostridial neurotoxins are still predominantly produced by fermentation processes using appropriate *Clostridium* strains. However, industrial production of clostridial neurotoxin from anaerobic *Clostridium* culturing is a cumbersome and time-consuming process. Due to the high toxicity of the final product, the procedure must be performed under strict containment. During the fermentation process, the single-chain precursors are proteolytically cleaved by an unknown clostridial protease to obtain the biologically active di-chain clostridial neurotoxin. The degree of neurotoxin activation by proteolytic cleavage varies between different strains and neurotoxin serotypes, which is a major consideration for the manufacture due to the requirement of neurotoxin preparations with a well-defined biological activity. Furthermore, during fermentation processes using *Clostridium* strains the clostridial neurotoxins are produced as protein complexes, in which the neurotoxic component is embedded by accessory proteins. These accessory proteins have no beneficial effect on biological activity or onset of effect or other pharmacological properties. They can however trigger an immune reaction in the patient, resulting in immunity against the clostridial neurotoxin. Manufacture of recombinant clostridial neurotoxins, which are not embedded by auxiliary proteins, might therefore be advantageous.

Methods for the recombinant expression of clostridial neurotoxins in *E. coli* are well known in the art (see, for example, WO 00/12728, WO 01/14570, or WO 2006/076902). Furthermore, clostridial neurotoxins have been expressed in eukaryotic expression systems, such as in *Pichia pastoris, Pichia methanolica, Saccharomyces cerevisiae*, insect cells and mammalian cells (see WO 2006/017749).

Recombinant clostridial neurotoxins may be expressed as single-chain precursors, which subsequently have to be proteolytically cleaved to obtain the final biologically active clostridial neurotoxin. Thus, clostridial neurotoxins may be expressed in high yield in rapidly-growing bacteria as relatively non-toxic single-chain polypeptides.

Furthermore, it might be advantageous to modify clostridial neurotoxin characteristics regarding biological activity, cell specificity, antigenic potential and duration of effect and onset of effect by genetic engineering to obtain recombinant neurotoxins with new therapeutic properties in specific clinical areas. Genetic modification of clostridial neurotoxins might allow altering the mode of action or expanding the range of therapeutic targets.

WO 96/39166 discloses analogues of botulinum toxin comprising amino acid residues which are more resistant to degradation in neuromuscular tissue.

Patent family based on WO 02/08268 (including family member U.S. Pat. No. 6,903,187) discloses a clostridial neurotoxin comprising a structural modification selected from addition or deletion of a leucine-based motif, which alters the biological persistence of the neurotoxin (see also: Fernández-Salas et al., Proc. Natl. Acad. Sci. U.S.A. 101 (2004) 3208-3213; Wang et al., J. Biol. Chem. 286 (2011) 6375-6385). Fernández-Salas et al. initially hypothesized that the increased persistence was due to the membrane-binding properties of the dileucine motif (see Fernández-Salas et al., loc. cit., p. 3211 and 3213). Wang et al. mention this membrane theory (see Wang et al., loc. cit., p. 6376, left column, last full paragraph, and p. 6383, first full paragraph of "Discussion"), but favor an alternative theory: the protection from degradation by proteolysis (see Wang et al., loc. cit., p. 6384, left column, lines 27ff).

WO 2015/132004 describes clostridial neurotoxins comprising a random coil domain, particularly wherein said random coil domain consists of alanine, serine and proline residues, and exhibiting an altered biological persistence.

A botulinum toxin variant exhibiting an increased duration of effect without a delayed onset of effect in neuromuscular tissue than naturally occurring botulinum toxins would be advantageous in order to reduce administration frequency and the incidence of neutralizing antibody generation since immunologic tolerance to botulinum toxin is correlated with cumulative doses.

Furthermore, BoNT serotypes naturally exhibiting a short duration of action could potentially be effectively used in clinical applications, if their biological persistence could be enhanced. Modified BoNT/E with an increased duration of action could potentially be used in patients exhibiting an immune reaction against BoNT/A. Moreover, BoNT/E was shown to induce a more severe block of pain mediator release from sensory neurons than BoNT/A. In clinical applications where BoNT/A provides only partial pain relief or in just a subset of patients, such as in the treatment of headaches, or where BoNT/E has been found to be more effective than BoNT/A but gives only short-term therapy, such as in the treatment of epilepsy, BoNT/E with an increased duration of effect might prove useful.

There is a strong demand to produce clostridial neurotoxins with an increased duration of effect without a delayed onset of effect, in order to allow for reduction of administration frequency and exploitation of the therapeutic potential of BoNT serotypes, which have so far been considered impractical for clinical application due to the short half-life of the respective clinically relevant effect. Ideally, the duration of effect of a particular clostridial neurotoxin could be adjusted in a tailor-made fashion in order to address any particular features and demands of a given indication, such as the amount of neurotoxin being administered, frequency of administration etc. To date, despite the progress that has already been made (see, in particular, WO 2015/132004), such aspects have not been solved satisfactorily.

OBJECTS OF THE INVENTION

It was an object of the invention to provide recombinant clostridial neurotoxins exhibiting an increased duration of effect without a delayed onset of effect, and to establish a reliable and accurate method for manufacturing and obtaining such recombinant clostridial neurotoxins. Such a method and novel precursor clostridial neurotoxins used in such methods would serve to satisfy the great need for recombinant clostridial neurotoxins exhibiting an increased duration of effect without a delayed onset of effect.

SUMMARY OF THE INVENTION

The naturally occurring botulinum toxin serotypes display highly divergent durations of effect, probably due to their distinct subcellular localization. BoNT/A exhibiting the longest persistence was shown to localize in the vicinity of the plasma membrane of neuronal cells, whereas the short-duration BoNT/E serotype is cytosolic. However, additional factors such as degradation, diffusion, and/or translocation rates might have a decisive impact on the differences in the duration of effect for the individual botulinum toxin serotypes.

So far, except for the approach described and claimed in WO 2015/132004, no generally applicable method for modifying clostridial neurotoxins in order to increase their duration of effect is available. Surprisingly, it has been found that recombinant clostridial neurotoxins having even better effects than those disclose in WO 2015/132004 can be obtained by cloning at least one specific sequence encoding a certain domain into a gene encoding a parental clostridial neurotoxin, and by subsequent heterologous expression of the generated construct in recombinant host cells.

Thus, in one aspect, the present invention relates to a recombinant clostridial neurotoxin comprising at least one domain wherein said domain comprises an amino acid sequence consisting of at least 50 amino acid residues, selected from proline, alanine, serine, threonine, glycine and glutamate residues.

In another aspect, the present invention relates to a composition, in particular to pharmaceutical composition, comprising the recombinant clostridial neurotoxin of the present invention.

In yet another aspect, the present invention relates to the use of the composition of the present invention for cosmetic treatment.

In yet another aspect, the present invention relates to a method for treating a patient comprising the step of administering a composition comprising the recombinant clostridial neurotoxin of the present invention.

In another aspect, the present invention relates to a method for the generation of the recombinant clostridial neurotoxin of the present invention, comprising the step of obtaining a recombinant nucleic acid sequence encoding a recombinant single-chain precursor clostridial neurotoxin by the insertion of one or more nucleic acid sequences each encoding said domain at one or two positions into a nucleic acid sequence encoding a parental clostridial neurotoxin.

In another aspect, the present invention relates to a recombinant single-chain precursor clostridial neurotoxin comprising one or two domains consisting of proline, alanine, serine, threonine, glycine and glutamate residues.

In another aspect, the present invention relates to a nucleic acid sequence encoding the recombinant single-chain precursor clostridial neurotoxin of the present invention.

In another aspect, the present invention relates to a method for obtaining the nucleic acid sequence of the present invention, comprising the step of inserting one or more nucleic acid sequences encoding said domain at one or two positions into a nucleic acid sequence encoding a parental clostridial neurotoxin.

In another aspect, the present invention relates to a vector comprising the nucleic acid sequence of the present invention, or the nucleic acid sequence obtainable by the method of the present invention.

In another aspect, the present invention relates to a recombinant host cell comprising the nucleic acid sequence of the present invention, the nucleic acid sequence obtainable by the method of the present invention, or the vector of the present invention.

In another aspect, the present invention relates to a method for producing the recombinant single-chain precursor clostridial neurotoxin of the present invention, comprising the step of expressing the nucleic acid sequence of the present invention, or the nucleic acid sequence obtainable by the method of the present invention, or the vector of the present invention in a recombinant host cell, or cultivating the recombinant host cell of the present invention under conditions that result in the expression of said nucleic acid sequence.

FIGURES

FIG. 1: Schematic presentation of a PASTGE-botulinum toxin A (PASTGE100-BoNT/A-PASTGE200).

Figure 2:
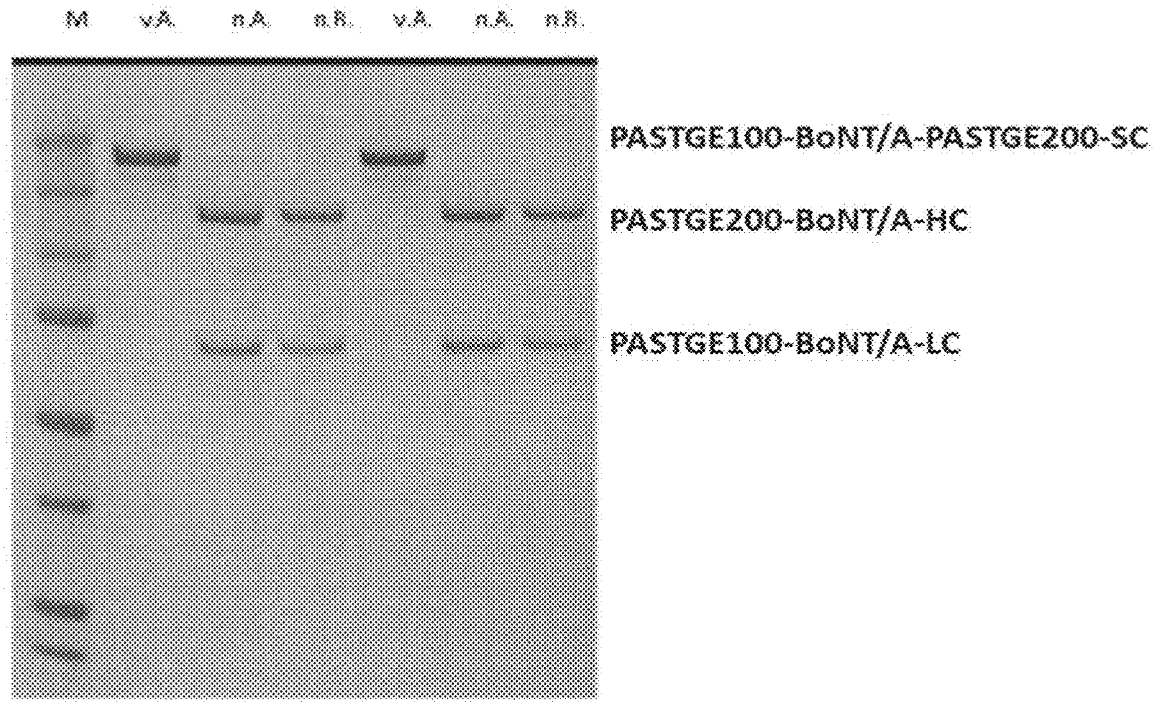

FIG. 2: SDS•PAGE of purified PASTGE100-BoNT/A-PASTGE200. Prior to applying the samples to the gel, β-mercaptoethanol was added. Lane "v.A." (before activation): purified, non-activated single-chain PASTGE100-BoNT/A-PASTGE200-SC. Lanes "n.A." (after activation) and "n.R." (after purification) show light chain (PASTGE100-LC) and heavy chain (PASTGE200-HC) obtained after activation by thrombin under reducing conditions.

Figure 3:
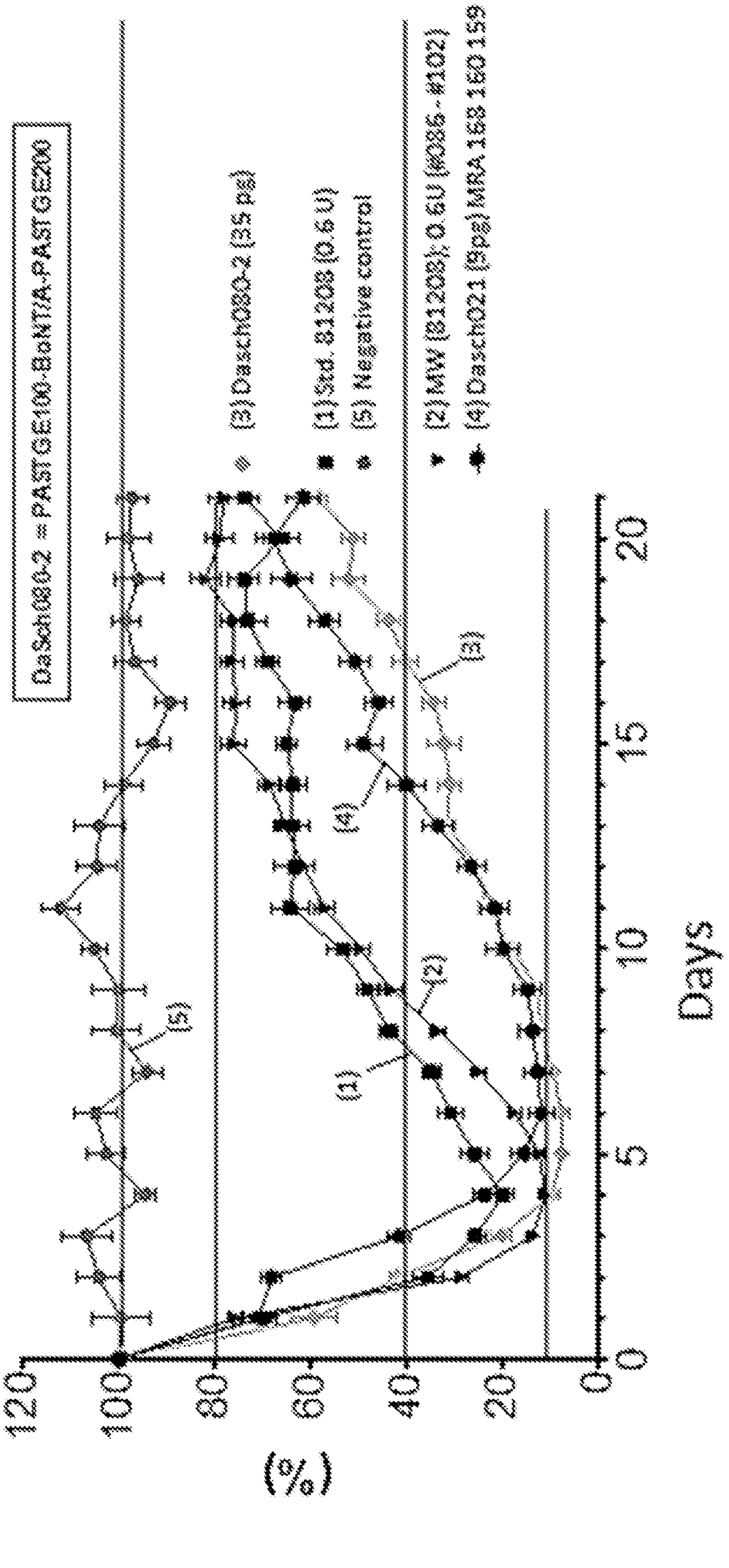

FIG. 3: Mouse running assay with PASTGE100-BoNT/A-PASTGE200:

♦:DaSch080-2 (PASTGE100-BoNT/A-PASTGE200) 35 pg were injected into the *M. gastrocnemius* of eight mice (volume 20 μl)

Std 81208(0.6 U), standard from Xeomin (3 pg) were injected into the *M. gastrocnemius* of eight mice (volume 20 μl)

▼: mean of standard (17 assays) from Xeomin® 81208 (0.6 U) (3 pg) DaSch021 (PAS100-rBoNT/A-PAS100) (9 pg) mean value of three assays Negative control

DETAILED DESCRIPTION OF THE INVENTION

The present invention may be understood more readily by reference to the following detailed description of the invention and the examples included therein.

In one aspect, the present invention relates to a recombinant clostridial neurotoxin comprising at least one domain wherein said domain comprises an amino acid sequence consisting of at least 50 amino acid residues, selected from proline, alanine, serine, threonine, glycine and glutamate residues.

In the context of the present invention, the term "clostridial neurotoxin" refers to a natural neurotoxin obtainable from bacteria of the class Clostridia, including *Clostridium tetani* and *Clostridium botulinum*, or to a neurotoxin obtainable from alternative sources, including from recombinant technologies or from genetic or chemical modification. Particularly, the clostridial neurotoxins have endopeptidase activity.

Clostridial neurotoxins are produced as single-chain precursors that are proteolytically cleaved by an unknown clostridial endoprotease within the loop region to obtain the biologically active disulfide-linked di-chain form of the neurotoxin, which comprises two chain elements, a functionally active light chain and a functionally active heavy chain, where one end of the light chain is linked to one end of the heavy chain not via a peptide bond, but via a disulfide bond.

In the context of the present invention, the term "clostridial neurotoxin light chain" refers to that part of a clostridial neurotoxin that comprises an endopeptidase activity responsible for cleaving one or more proteins that is/are part of the so-called SNARE-complex involved in the process resulting in the release of neurotransmitter into the synaptic cleft: In naturally occurring clostridial neurotoxins, the light chain has a molecular weight of approx. 50 kDa.

In the context of the present invention, the term "clostridial neurotoxin heavy chain" refers to that part of a clostridial neurotoxin that is responsible for entry of the neurotoxin into the neuronal cell: In naturally occurring clostridial neurotoxins, the heavy chain has a molecular weight of approx. 100 kDa.

In the context of the present invention, the term "functionally active clostridial neurotoxin chain" refers to a recombinant clostridial neurotoxin chain able to perform the biological functions of a naturally occurring *Clostridium botulinum* neurotoxin chain to at least about 50%, particularly to at least about 60%, to at least about 70%, to at least about 80%, and most particularly to at least about 90%, where the biological functions of clostridial neurotoxin chains include, but are not limited to, binding of the heavy chain to the neuronal cell, entry of the neurotoxin into a neuronal cell, release of the light chain from the di-chain neurotoxin, and endopeptidase activity of the light chain. Methods for determining a neurotoxic activity can be found, for example, in WO 95/32738, which describes the reconstitution of separately obtained light and heavy chains of tetanus toxin and botulinum toxin. Also cell-based assay methods as described for example in WO2009/114748, WO 2013/049508 and WO2014/207109.

In the context of the present invention, the term "about" or "approximately" means within 20%, alternatively within 10%, including within 5% of a given value or range. Alternatively, especially in biological systems, the term "about" means within about a log (i.e. an order of magnitude), including within a factor of two of a given value.

In the context of the present invention, the term "recombinant clostridial neurotoxin" refers to a composition comprising a clostridial neurotoxin that is obtained by expression of the neurotoxin in a heterologous cell such as *E. coli*, and including, but not limited to, the raw material obtained from a fermentation process (supernatant, composition after cell lysis), a fraction comprising a clostridial neurotoxin obtained from separating the ingredients of such a raw material in a purification process, an isolated and essentially pure protein, and a formulation for pharmaceutical and/or aesthetic use comprising a clostridial neurotoxin and additionally pharmaceutically acceptable solvents and/or excipients.

In the context of the present invention, the term "recombinant clostridial neurotoxin" further refers to a clostridial neurotoxin based on a parental clostridial neurotoxin additionally comprising a heterologous domain wherein this domain consists of proline, alanine, serine, threonine, glycine and glutamate residues, i.e. a domain that is not naturally occurring in said parental clostridial neurotoxin, in particular a synthetic domain, or a domain from a species other than *Clostridium botulinum*, in particular a domain from a human protein.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components, or groups thereof. The term "comprising" thus includes the more restrictive terms "consisting of" and "consisting essentially of".

In particular embodiments, said recombinant clostridial neurotoxin exhibits at least one domain comprising an amino acid sequence consisting of between 50 and 500 amino acid residues, more particularly between 70 and 300 amino acid residues, or between 80 and 120 amino acid residues, or between 180 and 220 amino acid residues, particularly 100 amino acid residues, 150 amino acid residues, or 200 amino acid residues.

Surprisingly, it has been found that the attachment of a domain consisting of proline, alanine, serine, threonine, glycine and glutamate residues is able to increase the duration of effect without a delayed onset of effect relative to an identical clostridial neurotoxin without said domain. A person skilled in the art would not expect such an effect. It has been shown in WO2015/132004 that the attachment of a neurotoxin with proline, alanine and serine residues could increase the duration of effect, however these data also showed that the onset of effect was significantly delayed. In the context of the present invention the attachment of a domain consisting of proline, alanine, serine, threonine, glycine and glutamate residues residues surprisingly leads to an increased duration of effect without a delayed onset of effect relative to an identical clostridial neurotoxin without said domain.

In particular embodiments, said recombinant clostridial neurotoxin exhibits at least one domain which is inserted at a position selected from (i) the N-terminus of the light chain of said recombinant clostridial neurotoxin; (ii) the C-terminus of the light chain of said recombinant clostridial neurotoxin; (iii) the N-terminus of the heavy chain of said recombinant clostridial neurotoxin; or (iv) the C-terminus of the heavy chain of said recombinant clostridial neurotoxin.

In particular embodiments, said recombinant clostridial neurotoxin exhibits one domain which is inserted at the N-terminus of the light chain of said recombinant clostridial neurotoxin and one domain which is inserted at the C-terminus of the heavy chain of said recombinant clostridial neurotoxin In particular embodiments, the sequence of said clostridial neurotoxin is selected from the sequence of (i) a *Clostridium botulinum* neurotoxin serotype A, B, C, D, E, F, and G, or (ii) from the sequence of a functional variant of a *Clostridium botulinum* neurotoxin of (i).

In the context of the present invention, the term "*Clostridium botulinum* neurotoxin serotype A, B, C, D, E, F, and G" refers to neurotoxins found in and obtainable from *Clostridium botulinum*. Currently, seven serologically distinct types, designated serotypes A, B, C, D, E, F, and G are known, including certain subtypes (e.g. A1, A2, A3, A4 and A5).

In the context of the present invention, the term "functional variant of a clostridial neurotoxin" refers to a neurotoxin that differs in the amino acid sequence and/or the nucleic acid sequence encoding the amino acid sequence from a clostridial neurotoxin, but is still functionally active. In the context of the present invention, the term "functionally active" refers to the property of a recombinant clostridial neurotoxin to exhibit a biological activity of at least about 20%, particularly to at least about 50%, at least about 70%, at least about 80%, and most particularly at least about 90% of the biological activity of a naturally occurring parental clostridial neurotoxin, i.e. a parental clostridial neurotoxin without said domain, where the biological functions include, but are not limited to, binding to the neurotoxin receptor, entry of the neurotoxin into a neuronal cell, release of the light chain from the di-chain neurotoxin, and endopeptidase activity of the light chain, and thus inhibition of neurotransmitter release from the affected nerve cell. In vivo assays for assessing biological activity include the mouse LD50 assay and the ex vivo mouse hemidiaphragm assay as described by Pearce et al. (Pearce 1994, Toxicol. Appl. Pharmacol. 128: 69-77) and Dressler et al. (Dressler 2005, Mov. Disord. 20:1617-1619, Keller 2006, Neuroscience 139: 629-637) or a cell-based assay as described in WO2009/114748, WO2014/207109 or WO 2013/049508. The biological activity is commonly expressed in Mouse Units (MU). As used herein, 1 MU is the amount of neurotoxic component, which kills 50% of a specified mouse population after intraperitoneal injection, i.e. the mouse i.p. LD50.

On the protein level, a functional variant will maintain key features of the corresponding clostridial neurotoxin, such as key residues for the endopeptidase activity in the light chain, or key residues for the attachment to the neurotoxin receptors or for translocation through the endosomal membrane in the heavy chain, but may contain one or more mutations comprising a deletion of one or more amino acids of the corresponding clostridial neurotoxin, an addition of one or more amino acids of the corresponding clostridial neurotoxin, and/or a substitution of one or more amino acids of the corresponding clostridial neurotoxin. Particularly, said deleted, added and/or substituted amino acids are consecutive amino acids. According to the teaching of the present invention, any number of amino acids may be added, deleted, and/or substituted, as long as the functional variant remains biologically active. For example, 1, 2, 3, 4, 5, up to 10, up to 15, up to 25, up to 50, up to 100, up to 200, up to 400, up to 500 amino acids or even more amino acids may be added, deleted, and/or substituted. Accordingly, a functional variant of the neurotoxin may be a biologically active fragment of a naturally occurring neurotoxin. This neurotoxin fragment may contain an N-terminal, C-terminal, and/or one or more internal deletion(s).

In another embodiment, the functional variant of a clostridial neurotoxin additionally comprises a signal peptide. Usually, said signal peptide will be located at the N-terminus of the neurotoxin. Many such signal peptides are known in the art and are comprised by the present invention. In particular, the signal peptide results in transport of the neurotoxin across a biological membrane, such as the membrane of the endoplasmic reticulum, the Golgi membrane or the plasma membrane of a eukaryotic or prokaryotic cell. It has been found that signal peptides, when attached to the neurotoxin, will mediate secretion of the neurotoxin into the supernatant of the cells. In certain embodiments, the signal peptide will be cleaved off in the course of, or subsequent to, secretion, so that the secreted protein lacks the N-terminal signal peptide, is composed of separate light and heavy chains, which are covalently linked by disulfide bridges, and is proteolytically active.

In particular embodiments, the functional variant has in its *clostridium* neurotoxin part a sequence identity of at least about 40%, at least about 50%, at least about 60%, at least about 70% or most particularly at least about 80%, and a sequence homology of at least about 60%, at least about 70%, at least about 80%, at least about 90%, or most particularly at least about 95% to the corresponding part in the parental clostridial neurotoxin. Methods and algorithms for determining sequence identity and/or homology, including the comparison of variants having deletions, additions, and/or substitutions relative to a parental sequence, are well known to the practitioner of ordinary skill in the art. The term "identity" as used herein refers to sequence identity characterized by determining the number of identical amino acids between two nucleic acid sequences or two amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. On the DNA level, the nucleic acid sequences encoding the functional homologue and the parental clostridial neurotoxin may differ to a larger extent due to the degeneracy of the genetic code. It is known that the usage of codons is different between prokaryotic and eukaryotic organisms. Thus, when expressing a prokaryotic protein such as a clostridial neurotoxin, in a eukaryotic expression system, it may be necessary, or at least helpful, to adapt the nucleic acid sequence to the codon usage of the expression host cell, meaning that sequence identity or homology may be rather low on the nucleic acid level.

In the context of the present invention, the term "variant" refers to a neurotoxin that is a chemically, enzymatically, or genetically modified derivative of a corresponding clostridial neurotoxin, including chemically or genetically modified neurotoxin from *C. botulinum*, particularly of *C. botulinum* neurotoxin serotype A, C or E. A chemically modified derivative may be one that is modified by pyruvation, phosphorylation, sulfatation, lipidation, pegylation, glycosylation and/or the chemical addition of an amino acid or a polypeptide comprising between 2 and about 100 amino acids, including modification occurring in the eukaryotic host cell used for expressing the derivative. An enzymatically modified derivative is one that is modified by the activity of enzymes, such as endo- or exoproteolytic enzymes, including modification by enzymes of the eukaryotic host cell used for expressing the derivative. As pointed out above, a genetically modified derivative is one that has been modified by deletion or substitution of one or more amino acids contained in, or by addition of one or more amino acids (including polypeptides comprising between 2 and about 100 amino acids) to, the amino acid sequence of said clostridial neurotoxin. Methods for designing and constructing such chemically or genetically modified derivatives and for testing of such variants for functionality are well known to anyone of ordinary skill in the art.

In particular embodiments, said recombinant clostridial neurotoxin exhibits at least one domain comprising a plurality of amino acid repeats, wherein said repeats consist of proline, alanine, serine, threonine, glycine and glutamate residues and wherein no more than six consecutive amino acid residues are identical.

In particular embodiments, the proline residues comprised in at least one of said domain constitute more than 4% and less than 40% of the amino acids of said domain.

In particular embodiments, said recombinant clostridial neurotoxin exhibits at least one domain comprising the following amino acid sequence:

(SEQ ID NO: 1)

SPAGSPTSTEEGTSESATPESGPGTSTEPSEGSAPGSPAGSPTSTEEGT

STEPSEGSAPGTSTEPSEGSAPGTSESATPESGPGSEPATSGSETPGSE

PA.

In particular embodiments, said recombinant clostridial neurotoxin exhibits at least one domain comprising the following amino acid sequence:

(SEQ ID NO: 2)

SPAGSPTSTEEGTSESATPESGPGTSTEPSEGSAPGSPAGSPTSTEEGT

STEPSEGSAPGTSTEPSEGSAPGTSESATPESGPGSEPATSGSETPGSE

PATSGSETPGSPAGSPTSTEEGTSESATPESGPGTSTEPSEGSAPGTST

EPSEGSAPGSPAGSPTSTEEGTSTEPSEGSAPGTSTEPSEGSAPGTSES

ATPE.

In particular embodiments, said recombinant clostridial neurotoxin comprises both a domain consisting of the amino acid sequence according to SEQ ID NO: 1 and a domain consisting of the amino acid sequence according to SEQ ID NO: 2.

In particular embodiments, said recombinant clostridial neurotoxin comprises i) the domain consisting of the amino acid sequence according to SEQ ID NO: 1, wherein this domain is inserted at the N-terminus of the light chain of said recombinant clostridial neurotoxin and ii) the domain consisting of the amino acid sequence according to SEQ ID NO: 2, wherein this domain is inserted at the C-terminus of the heavy chain of said recombinant clostridial neurotoxin.

In particular embodiments, said recombinant clostridial neurotoxin shows an increased duration of effect without a delayed onset of effect relative to an identical clostridial neurotoxin without said domain(s).

In the context of the present invention, the term "increased duration of effect" or "increased duration of action" refers to a longer lasting denervation mediated by a clostridial neurotoxin of the present invention. For example, as disclosed herein, administration of a disulfide-linked di-chain clostridial neurotoxin comprising a domain according to the invention results in localized paralysis for a longer period of time relative to administration of an identical disulfide-linked di-chain clostridial neurotoxin without the domain according to the present invention.

In the context of the present invention, the term "increased duration of effect/action" is defined as a more than about 20%, particularly more than about 50%, more particularly more than about 90% increased duration of effect of the recombinant neurotoxin of the present invention relative to the identical neurotoxin without the domain according to the invention.

In the context of the present invention the term "maximum paralytic effect" refers to a value of 80-90% reduction of the initial running distance.

For example, an "increased duration of effect/action" can be determined using the "Mouse Running Assay". The "Mouse Running Assay" is well-known to the person skilled in the art and measures the daily running distance of a mouse in a treadmill after a botulinum neurotoxin was injected into the *M. gastrocnemius* (see Keller J E. Recovery from botulinum neurotoxin poisoning in vivo. Neuroscience. 2006 May 12; 139(2):629-37). The distance which a mouse is able to run in the treadmill the day before the botulinum neurotoxin is injected is used as comparison and is set as 100%. A daily running distance of no more than 80% of the initial running distance is regarded as paralysis of the muscle. The duration of effect is determined by the time period between the time point attaining a half-maximal paralysis, i.e. about 40% of the initial running distance, and the time point when paralysis reaches recovery, i.e. about 40% of the initial running distance. If this time period is 2 days longer compared with the standard (wildtype BoNT) provided that the mutated BoNT exhibits a similar potency i.e shows a similar maximal paralysis (reduction of the running distance) of about 80-90%, the botulinum neurotoxin is considered to exhibit an "increased duration of effect/action".

In the context of the present invention the term "denervation" refers to denervation resulting from administration of a chemodenervating agent, for example a neurotoxin.

In the context of the present invention, the term "localized denervation" or "localized paralysis" refers to denervation of a particular anatomical region, usually a muscle or a group of anatomically and/or physiologically related muscles, which results from administration of a chemodenervating agent, for example a neurotoxin, to the particular anatomical region.

Without wishing to be bound by theory, the recombinant clostridial neurotoxins of the present invention might show increased biological half-life, reduced degradation rates, decreased diffusion rates, increased uptake by neuronal cells, and/or modified intracellular translocation rates, in each case relative to an identical parental clostridial neurotoxin without the domain according to the invention.

In the context of the present invention, the term "without a delayed onset of effect" refers to the starting point of denervation mediated by a clostridial neurotoxin of the present invention. For example, as disclosed herein, administration of a disulfide-linked di-chain clostridial neurotoxin comprising a domain consisting of proline, alanine, serine, threonine, glycine and glutamate residues results in localized paralysis at a comparable point in time relative to administration of a wildtype clostridial neurotoxin.

For example, an "onset of effect without a delay" can be determined using the "Mouse Running Assay". The "Mouse Running Assay" is well-known to the person skilled in the art as described above. If a maximum paralytic effect of 80-90% reduction of the running distance is attained earlier than four days post injection of a botulinum neurotoxin (i.e. similar to the wildtype BoNT), the botulinum neurotoxin is considered to exhibit an "onset of effect without delay", provided that the mutated BoNT exhibits a similar potency i.e shows a similar maximal paralysis (reduction of the running distance) of about 80-90%.

In another aspect, the present invention relates to a pharmaceutical or cosmetic composition comprising the recombinant clostridial neurotoxin of the present invention. For preparing a pharmaceutical preparation comprising a clostridial neurotoxin the toxin can be formulated by various techniques dependent on the desired application purposes which are known in the art. For example, the (biologically active) botulinum neurotoxin polypeptide can be used in combination with one or more pharmaceutically acceptable carriers as a pharmaceutical composition. The pharmaceutically acceptable carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are glycerol, phosphate buffered saline solution, water, emulsions, various types of wetting agents, and the like. Suitable carriers comprise those mentioned above and others well known in the art, see, e.g., Remington's Pharmaceutical Sciences, Mack Publishing Company, Easton, Pa. In an aspect, the pharmaceutical composition can be dissolved in a diluent, prior to administration. The diluent is also selected so as not to affect the biological activity of the Neurotoxin product. Examples of such diluents are distilled water or physiological saline. In addition, the pharmaceutical composition or formulation may also include other carriers or non-toxic, non-therapeutic, non-immunogenic stabilizers and the like. Thus, the formulated Neurotoxin product can be present, in an aspect, in liquid or lyophilized form. In an aspect, it can be present together with glycerol, protein stabilizers (HSA) or non-protein stabilizers such as polyvinyl pyrrolidone (PVP), hyaluronic acid or free amino acids. In an aspect, suitable non-proteinaceous stabilizers are disclosed in WO 2005/007185 or WO 2006/020208. The formulated Neurotoxin product may be used for human or animal therapy of various diseases or disorders in a therapeutically effective dose or for cosmetic purposes.

In particular embodiments, the recombinant clostridial neurotoxin of the present invention or the pharmaceutical composition of the present invention is for use in the treatment of a disease or condition taken from the list of: cervical dystonia (spasmodic torticollis), blepharospasm, severe primary axillary hyperhidrosis, achalasia, lower back pain, benign prostate hypertrophy, chronic focal painful neuropathies, migraine and other headache disorders.

Additional indications where treatment with botulinum neurotoxins is currently under investigation and where the pharmaceutical composition of the present invention may be used, include pediatric incontinence, incontinence due to overactive bladder, and incontinence due to neurogenic bladder, anal fissure, spastic disorders associated with injury or disease of the central nervous system including trauma, stroke, multiple sclerosis, Parkinson's disease, or cerebral palsy, focal dystonias affecting the limbs, face, jaw or vocal cords, temporomandibular joint (TMJ) pain disorders, diabetic neuropathy, wound healing, excessive salivation, vocal cord dysfunction, reduction of the Masseter muscle for decreasing the size of the lower jaw, treatment and prevention of chronic headache and chronic musculoskeletal pain, treatment of snoring noise, assistance in weight loss by increasing the gastric emptying time.

Most recently, clostridial neurotoxins have been evaluated for the treatment of other new indications, for example painful keloid, diabetic neuropathic pain, refractory knee pain, trigeminal neuralgia trigger-zone application to control pain, scarring after cleft-lip surgery, cancer and depression.

In yet another aspect, the present invention relates to the use of the composition of the present invention for cosmetic treatment.

Thus, in another aspect, the present invention relates to a method of cosmetically treating a patient, comprising the step of administering a composition comprising a recombinant clostridial neurotoxin according to the present invention to a patient desiring such cosmetic treatment.

In the context of the present invention, the term "cosmetic treatment" relates to uses in cosmetic or aesthetic applications, such as the treatment of wrinkles, crow's feet, glabella frown lines, reduction of the masseter muscle, reduction of the calves, removing of facial asymmetries etc.

In another aspect, the present invention relates to a method for the generation of the recombinant clostridial neurotoxin of the present invention, comprising the step of obtaining a recombinant nucleic acid sequence encoding a recombinant single-chain precursor clostridial neurotoxin by the insertion of a nucleic acid sequence encoding said domain consisting of proline, alanine, serine, threonine, glycine and glutamate residues into a nucleic acid sequence encoding a parental clostridial neurotoxin.

In the context of the present invention, the term "recombinant nucleic acid sequence" refers to a nucleic acid, which has been generated by joining genetic material from two different sources.

In the context of the present invention, the term "single-chain precursor clostridial neurotoxin" refers to a single-chain precursor for a disulfide-linked di-chain clostridial neurotoxin, comprising a functionally active clostridial neurotoxin light chain, a functionally active neurotoxin heavy chain, and a loop region linking the C-terminus of the light chain with the N-terminus of the heavy chain.

In the context of the present invention, the term "recombinant single-chain precursor clostridial neurotoxin" refers to a single-chain precursor clostridial neurotoxin comprising a heterologous domain, i.e. a domain from a species other than *Clostridium botulinum.*

In particular embodiments, the recombinant single-chain precursor clostridial neurotoxin comprises a protease cleavage site in said loop region.

Single-chain precursor clostridial neurotoxins have to be proteolytically cleaved to obtain the final biologically active clostridial neurotoxins. Proteolytic cleavage may either occur during heterologous expression by host cell enzymes, or by adding proteolytic enzymes to the raw protein material isolated after heterologous expression. Naturally occurring clostridial neurotoxins usually contain one or more cleavage signals for proteases which post-translationally cleave the single-chain precursor molecule, so that the final di- or multimeric complex can form. At present, clostridial neurotoxins are still predominantly produced by fermentation processes using appropriate *Clostridium* strains. During the fermentation process, the single-chain precursors are proteolytically cleaved by an unknown clostridial protease to obtain the biologically active di-chain clostridial neurotoxin. In cases, where the single-chain precursor molecule is the precursor of a protease, autocatalytic cleavage may occur. Alternatively, the protease can be a separate non-clostridial enzyme expressed in the same cell. WO 2006/076902 describes the proteolytic cleavage of a recombinant clostridial neurotoxin single-chain precursor at a heterologous recognition and cleavage site by incubation of the *E. coli* host cell lysate. The proteolytic cleavage is carried out by an unknown *E. coli* protease. In certain applications of recombinant expression, modified protease cleavage sites have been introduced recombinantly into the interchain region between the light and heavy chain of clostridial toxins, e.g. protease cleavage sites for human thrombin or non-human proteases (see WO 01/14570).

In particular embodiments, the protease cleavage site is a site that is cleaved by a protease selected from the list of: thrombin, trypsin, enterokinase, factor Xa, plant papain, insect papain, crustacean papain, enterokinase, human rhinovirus 3C protease, human enterovirus 3C protease, tobacco etch virus protease, Tobacco Vein Mottling Virus, subtilisin and caspase 3.

In a particular embodiment, the recombinant single-chain precursor clostridial neurotoxin further comprises a binding tag, particularly selected from the group comprising: glutathione-S-transferase (GST), maltose binding protein (MBP), a His-tag, a Strep-tag, or a FLAG-tag.

In the context of the present invention, the term "parental clostridial neurotoxin" refers to an initial clostridial neurotoxin without a heterologous domain consisting of proline, alanine, serine, threonine, glycine and glutamate residues, selected from a natural clostridial neurotoxin, a functional variant of a natural clostridial neurotoxin or a chimeric clostridial neurotoxin, wherein the clostridial neurotoxin light chain and heavy chain are from different clostridial neurotoxin serotypes.

In particular embodiments, the method for the generation of the recombinant clostridial neurotoxin of the present invention further comprises the step of heterologously expressing said recombinant nucleic acid sequence in a host cell, particularly in a bacterial host cell, more particularly in an *E. coli* host cell.

In certain embodiments, the *E. coli* cells are selected from *E. coli* XL1-Blue, Nova Blue, TOP10, XL10-Gold, BL21, and K12.

In particular embodiments, the method for the generation of the recombinant clostridial neurotoxin of the present invention additionally comprises at least one of the steps of (i) generating a disulfide-linked di-chain recombinant clostridial neurotoxin comprising said domain consisting of proline, alanine, serine, threonine, glycine and glutamate residues by causing or allowing contacting of said recombinant single-chain precursor clostridial neurotoxin with an endoprotease and (ii) purification of said recombinant single-chain precursor clostridial neurotoxin or said disulfide-linked di-chain recombinant clostridial neurotoxin by chromatography.

In particular embodiments, the recombinant single-chain precursor clostridial neurotoxin, or the recombinant disulfide-linked di-chain clostridial neurotoxin, is purified after expression, or in the case of the recombinant disulfide-linked di-chain clostridial neurotoxin, after the cleavage reaction. In particular such embodiments, the protein is purified by chromatography, particularly by immunoaffinity chromatography, or by chromatography on an ion exchange matrix, a hydrophobic interaction matrix, or a multimodal chromatography matrix, particularly a strong ion exchange matrix, more particularly a strong cation exchange matrix.

In the context of the present invention, the term "causing . . . contacting of said recombinant single-chain precursor clostridial neurotoxin . . . with an endoprotease" refers to an active and/or direct step of bringing said neurotoxin and said endoprotease in contact, whereas the term "allowing contacting of a recombinant single-chain precursor clostridial neurotoxin . . . with an endoprotease" refers to an indirect step of establishing conditions in such a way that said neurotoxin and said endoprotease are getting in contact to each other.

In the context of the present invention, the term "endoprotease" refers to a protease that breaks peptide bonds of non-terminal amino acids (i.e. within the polypeptide chain). As they do not attack terminal amino acids, endoproteases cannot break down peptides into monomers.

In particular embodiments, cleavage of the recombinant single-chain precursor clostridial neurotoxin is near-complete.

In the context of the present invention, the term "near-complete" is defined as more than about 95% cleavage, particularly more than about 97.5%, more particularly more than about 99% as determined by SDS-PAGE and subsequent Western Blot or reversed phase chromatography.

In particular embodiments, cleavage of the recombinant single-chain precursor clostridial neurotoxin occurs at a heterologous cleavage signal located in the loop region of the recombinant precursor clostridial neurotoxin.

In particular embodiments, the cleavage reaction is performed with crude host cell lysates containing said single-chain precursor protein.

In other particular embodiments, the single-chain precursor protein is purified or partially purified, particularly by a first chromatographic enrichment step, prior to the cleavage reaction.

In the context of the present invention, the term "purified" relates to more than about 90% purity. In the context of the present invention, the term "partially purified" relates to purity of less than about 90% and an enrichment of more than about two fold.

In another aspect, the present invention relates to a recombinant single-chain clostridial neurotoxin, which is a precursor for the recombinant clostridial neurotoxin of the present invention Thus, in such aspect, the present invention relates to a recombinant single-chain precursor clostridial neurotoxin comprising at least one domain consisting of proline, alanine, serine, threonine, glycine and glutamate residues.

In another aspect, the present invention relates to a nucleic acid sequence encoding the recombinant single-chain clostridial neurotoxin of the present invention, particularly a nucleic acid sequence as found in SEQ ID NO: 3 (see Table 1).

In another aspect, the present invention relates to a method for obtaining the nucleic acid sequence of the present invention, comprising the step of inserting a nucleic acid sequence encoding said domain into a nucleic acid sequence encoding a parental clostridial neurotoxin.

In another aspect, the present invention relates to a vector comprising the nucleic acid sequence of the present invention, or the nucleic acid sequence obtainable by the method of the present invention.

In another aspect, the present invention relates to a recombinant host cell comprising the nucleic acid sequence of the present invention, the nucleic acid sequence obtainable by the method of the present invention, or the vector of the present invention.

In another aspect, the present invention relates to a method for producing the recombinant single-chain precursor clostridial neurotoxin of the present invention, comprising the step of expressing the nucleic acid sequence of the present invention, or the nucleic acid sequence obtainable by the method of the present invention, or the vector of the present invention in a recombinant host cell, or cultivating the recombinant host cell of the present invention under conditions that result in the expression of said nucleic acid sequence.

EXAMPLES

Example 1: Generation and Purification of a PASTGE100-BoNT/A-PASTGE200

The nucleic acid construct encoding two "PASTGE" modules comprising additional 100 and 200 amino acid residues respectively built from the amino acids proline, alanine, serine, threonine, glycine and glutamate residues was synthetically produced. By using restriction enzymes NdeI and SwaI for PASTGE100 and BglII and AatII for PASTGE200 the corresponding gene module was inserted at the N-terminus and C-terminus of recombinant BoNT/A (PASTGE100-BoNT/A-PASTGE200), wherein the linker exhibited a thrombin cleavage site sequence (FIG. 1). The correct cloning was verified by sequencing.

Expression was performed in expression strain *E. coli* Bl21. Purification was done using a combination of his affinity, ion exchange and size exclusion chromatography, followed by activation using thrombin. FIG. 2 summarizes the results of purification and activation.

Example 2: Duration of Effect and Onset of Effect of PASTGE100-BoNT/A-PASTGE200 in a "Mouse Running Assay"

Equipotent dosages of PASTGE100-BoNT/A-PASTGE200 (35 pg) or Xeomin® (9 pg) were injected into the *M. gastrocnemius* of eight mice in comparison to standard Xeomin® and to a dosage of a different modified BoNT (PAS100-rBoNT/A-PAS100) having two "PAS" modules each comprising 100 amino acid residues built from the amino acids proline, alanine and serine. The mice had been trained in a treadmill. The daily running distance in the treadmill was measured over 20 days. The paralysis caused by the toxins was plotted as percentage of the running distance on the day before the injection, which was set as 100%, against the time (see FIG. 3).

The injection of PASTGE100-BoNT/A-PASTGE200 resulted in a maximum paralysis after about 3 days which is comparable to the control group treated with Xeomin. Thus, the onset of effective paralysis was about the same.

During the recovery phase the running distance of the control group (mean of standard (17 assays) from Xeomin®) reached a value of 40% of the starting value 7 days after half-maximum paralysis was observed (day 9), whereas the group treated with PASTGE100-BoNT/A-PASTGE200 reached that value 15 days after half-maximum paralysis (day 17). Thus, the duration of effective paralysis was significantly extended.

TABLE 1

| Sequences |
|---|
| SEQ ID NO 1 (PASTGE100)<br>SPAGSPTSTEEGTSESATPESGPGTSTEPS<br>EGSAPGSPAGSPTSTEEGTSTEPSEGSAPG<br>TSTEPSEGSAPGTSESATPESGPGSEPATS<br>GSETPGSEPA |
| SEQ ID NO 2: (PASTGE200)<br>SPAGSPTSTEEGTSESATPESGPGTSTEPSEGSAPGSPAGSPTSTEEGTSTEPSEGSAPG<br>TSTEPSEGSAPGTSESATPESGPGSEPATSGSETPGSEPATSGSETPGSPAGSPTSTEEG<br>TSESATPESGPGTSTEPSEGSAPGTSTEPSEGSAPGSPAGSPTSTEEGTSTEPSEGSAPG<br>TSTEPSEGSAPGTSESATPE |
| SEQ ID NO 3: PASTGE100-BoNT/A- PASTGE 200 (nucleic acid sequence)<br>ATGGGTAGCAGCCATCATCATCACCATCATGGTAGCCTGGTTCCGCGTAGCTCTTCTCCG<br>GCTGGGTCTCCAACATCGACTGAAGAGGGTACGTCTGAGAGTGCTACACCCGAGAGCGGT<br>CCAGGCACATCCACGGAGCCATCCGAAGGGTCAGCGCCCGGAAGCCCGGCGGGTTCCCCG<br>ACATCGACTGAGGAGGGCACCTCAACAGAACCTAGCGAGGGTAGTGCACCGGGGACCAGC<br>ACTGAGCCCTCCGAAGGCTCCGCGCCAGGGACAAGTGAGTCCGCAACGCCAGAGAGCGGC<br>CCAGGCAGCGAGCCTGCCACGAGTGGGTCAGAGACGCCGGGGTCAGAACCTGCGCCATTT<br>GTGAACAAGCAGTTTAACTATAAGGACCCGGTGAACGGTGTGGATATCGCGTATATCAAA<br>ATCCCGAATGCGGGCCAGATGCAACCAGTCAAGGCGTTCAAGATTCATAACAAGATTTGG<br>GTTATTCCGGAACGTGATACCTTCACCAATCCGGAAGAAGGCGATTTAAATCCGCCGCCA<br>GAAGCCAAACAAGTGCCGGTGAGCTACTATGATAGCACGTATCTTAGCACCGATAATGAA<br>AAAGACAATTACCTGAAGGGCGTGACCAAGTTGTTCGAGCGCATCTACAGTACCGACTTA<br>GGCCGCATGTTGTTGACGAGCATCGTTCGCGGTATCCCGTTCTGGGGCGGCTCGACCATT<br>GATACCGAGTTGAAAGTCATTGACACGAACTGTATCAATGTTATCCAACCGGACGGCAGT<br>TATCGCAGCGAGGAGTTAAATTTGGTCATCATCGGTCCAAGCGCAGATATTATTCAGTTC<br>GAATGCAAGAGCTTCGGCCATGAGGTCTTGAATTTGACGCGCAACGGTTACGGCAGCACC<br>CAATACATCCGCTTTAGCCCGGATTTCACCTTTGGCTTCGAGGAGAGCTTGGAGGTGGAC<br>ACCAACCCGCTGTTAGGTGCCGGCAAATTCGCAACCGACCCGGCAGTGACGTTGGCGCAC<br>GAATTGATTCATGCGGGTCACCGCTTATACGGTATCGCGATCAATCCGAATCGCGTCTTT<br>AAAGTCAATACCAACGCGTACTACGAAATGAGCGGCTTAGAGGTTAGCTTTGAAGAATTA<br>CGCACCTTCGGTGGCCACGACGCCAAGTTCATCGACAGCCTGCAGGAAAATGAGTTCCGC<br>TTGTACTATTACAATAAATTCAAGGACATCGCGAGCACCTTAAATAAAGCAAAGAGCATT<br>GTGGGCACCACCGCAAGCTTGCAGTACATGAAGAACGTATTTAAGGAAAAATATTTGTTG<br>TCGGAGGATACCAGCGGGAAATTCAGCGTCGATAAGCTGAAATTCGACAAATTGTATAAA<br>ATGCTGACCGAGATTTACACCGAGGATAACTTCGTCAAGTTTTTTAAGGTGTTAAATCGT |

TABLE 1-continued

| Sequences |
|---|
| AAGACCTATTTAAACTTTGATAAAGCGGTGTTTAAAATTAATATCGTGCCGAAGGTGAAT<br>TACACCATCTACGATGGTTTCAATTTACGCAACACGAATCTGGCGGCGAATTTTAATGGC<br>CAAAACACCGAAATTAACAACATGAACTTTACGAAGTTAAAGAATTTCACGGGCTTATTC<br>GAATTCTACAAGTTATTATGCGTGCGCGGCATCATTACCAGCAAGGCAGGTGCGGGCAAG<br>TCCTTGGTTCCGCGTGGCAGCGCCGGCGCCGGCGCGCTCAATGATCTGTGTATTAAAGTC<br>AATAACTGGGACCTGTTCTTCAGCCCGAGCGAGGATAACTTTACCAACGACTTAAACAAA<br>GGCGAGGAGATCACGAGCGATACGAACATCGAGGCGGCGGAGGAAAATATTAGCCTGGAC<br>CTCATTCAGCAGTACTATCTGACGTTCAATTTTGACAATGAGCCGGAGAACATCAGCATT<br>GAAAATCTCAGCAGCGACATCATCGGTCAGTTGGAACTGATGCCGAACATTGAACGCTTT<br>CCGAACGGCAAAAAATATGAACTGGACAAGTATACCATGTTCCATTACTTACGCGCACAG<br>GAATTTGAGCACGGCAAGAGCCGCATTGCGCTGACCAATAGCGTTAACGAGGCCTTGTTA<br>AATCCGAGCCGTGTCTACACGTTCTTCAGCAGCGATTATGTCAAAAAAGTGAACAAGGCG<br>ACCGAAGCCGCGATGTTTTTGGGCTGGGTCGAGCAATTGGTTTACGATTTTACCGACGAA<br>ACCAGCGAGGTGAGCACGACCGACAAAATTGCAGATATCACCATCATCATTCCGTACATC<br>GGTCCGGCGCTCAATATCGGCAATATGTTATACAAGGACGACTTTGTGGGCGCGCTGATC<br>TTTAGCGGCGCGGTTATCTTATTAGAATTCATCCCGGAGATCGCAATCCCGGTCTTGGGC<br>ACCTTTGCGTTGGTGAGCTATATCGCGAATAAAGTGCTCACGGTCCAAACCATCGATAAC<br>GCGCTCAGCAAGCGTAATGAGAAATGGGACGAGGTTTATAAGTATATCGTGACCAACTGG<br>TTAGCAAAAGTCAATACGCAGATCGATCTCATCCGCAAAAAAATGAAAGAAGCCTTGGAA<br>AATCAAGCGGAGGCAACCAAAGCCATCATTAATTACCAGTATAACCAATATACCGAAGAA<br>GAAAAAAACAATATCAACTTCAATATCGATGATTTGAGCAGCAAACTGAACGAGAGCATT<br>AACAAAGCGATGATTAACATCAACAAGTTCTTGAATCAATGCAGCGTGAGCTATCTCATG<br>AACAGCATGATCCCGTATGGCGTCAAACGCTTGGAAGATTTTGACGCCAGCCTGAAAGAT<br>GCGCTCCTCAAGTATATTTATGACAACCGCGGCACCCTCATTGGCCAGGTGGACCGCTTG<br>AAGGATAAAGTGAACAATACGCTCAGCACGGATATCCCGTTCCAGCTGAGCAAGTACGTC<br>GACAACCAGCGCTTACTGAGCACCTTTACCGAGTATATCAAGAACATCATTAATACCAGC<br>ATCCTCAACTTGCGCTATGAGAGCAATCACCTGATCGACCTCAGCCGCTACGCCAGCAAG<br>ATCAACATCGGCAGCAAGGTCAATTTCGACCCGATCGATAAGAATCAGATCCAATTGTTT<br>AACCTGGAAAGCAGCAAGATCGAGGTTATCTTGAAGAACGCGATTGTGTACAACAGCATG<br>TACGAGAACTTTAGCACGAGCTTCTGGATTCGTATCCCGAAGTATTTCAATAGCATTAGC<br>CTGAATAACGAATATACCATTATCAACTGCATGGAAAATAATAGCGGCTGGAAGGTGAGC<br>TTAAATTACGGCGAGATCATTTGGACCTTACAGGATACCCAAGAAATCAAACAGCGCGTC<br>GTCTTTAAGTATAGCCAGATGATCAACATCAGCGATTACATCAACCGCTGGATCTTCGTG<br>ACCATCACCAATAATCGCTTGAATAATAGCAAGATTTACATCAATGGTCGCTTGATTGAT<br>CAAAAACCGATCAGCAATCTCGGTAATATCCATGCCAGCAATAACATCATGTTTAAGTTA<br>GACGGTTGCCGCGATACCCACCGCTATATCTGGATCAAGTATTTTAACTTATTTGATAAG<br>GAACTCAACGAAAAGGAAATTAAAGACTTATATGACAATCAGAGCAATAGCGGCATCCTG<br>AAGGATTTCTGGGGCGACTACCTGCAGTACGATAAGCCGTACTATATGTTGAACTTGTAT<br>GACCCGAACAAATATGTCGATGTGAACAATGTGGGTATTCGTGGCTATATGTACTTAAAG<br>GGCCCGCGTGGTAGCGTGATGACCACGAATATTTACTTAAACAGCAGCTTATACCGCGGC<br>ACGAAGTTTATTATCAAGAAGTATGCCAGCGGCAACAAGGACAATATCGTCCGCAACAAC<br>GACCGTGTGTATATTAACGTGGTGGTGAAGAATAAAGAGTACCGCTTGGCCACGAATGCG<br>AGCCAGGCGGGCGTGGAAAAAATCTTGAGCGCGTTGGAGATCCCGGACGTCGGCAACCTC<br>AGCCAGGTTGTGGTGATGAAGTCTAAAAACGACCAGGGCATCACGAACAAGTGCAAAATG<br>AATTTGCAAGATAACAACGGCAACGACATCGGCTTTATTGGTTTTCACCAGTTCAATAAC<br>ATCGCCAAACTCGTGGCCAGCAATTGGTATAACCGCCAAATTGAACGCAGCAGCCGCACG<br>CTCGGCTGTAGCTGGGAGTTCATCCCGGTGGACGATGGCTGGGGCGAGCGCCCGCTCTCT<br>CCGGCGGGTTCTCCGACCTCTACCGAAGAAGGTACCTCTGAATCTGCGACCCCGGAATCT<br>GGTCCGGGTACCTCTACCGAACCGTCTGAAGGTTCTGCGCCGGGTTCTCCGGCGGGTTCT<br>CCGACCTCTACCGAAGAAGGTACCTCTACCGAACCGTCTGAAGGTTCTGCGCCGGGTACC<br>TCTACCGAACCGTCTGAAGGTTCTGCGCCGGGTACCTCTGAATCTGCGACCCCGGAATCT<br>GGTCCGGGTTCTGAACCGGCGACCTCTGGTTCTGAAACCCCGGGTTCTGAACCGGCGACC<br>TCTGGTTCTGAAACCCCGGGTTCTCCGGCGGGTTCTCCGACCTCTACCGAAGAAGGTACC<br>TCTGAATCTGCGACCCCGGAATCTGGTCCGGGTACCTCTACCGAACCGTCTGAAGGTTCT<br>GCGCCGGGTACCTCTACCGAACCGTCTGAAGGTTCTGCGCCGGGTTCTCCGGCGGGTTCT<br>CCGACCTCTACCGAAGAAGGTACCTCTACCGAACCGTCTGAAGGTTCTGCGCCGGGTACC<br>TCTACCGAACCGTCTGAAGGTTCTGCGCCGGGTACCTCTGAATCTGCGACCCCGGAAGGA<br>GATCTGGTGCCACGCGGTTCCGCGAATTCGAGCTCCGTCGACAAGCTTTGGAGCCACCCG<br>CAGTTCGAAAAATAA |
| SEQ ID NO 4: PASTGE100-BoNT/A- PASTGE 200 (amino acid sequence)<br>MGSSHHHHHHGSLVPRSSSPAGSPTSTEEGTSESATPESGPGTSTEPSEGSAPGSPAGSP<br>TSTEEGTSTEPSEGSAPGTSTEPSEGSAPGTSESATPESGPGSEPATSGSETPGSEPAPF<br>VNKQFNYKDPVNGVDIAYIKIPNAGOMOPVKAFKIHNKIWVIPERDTFTNPEEGDLNPPP<br>EAKQVPVSYYDSTYLSTDNEKDNYLKGVTKLFERIYSTDLGRMLLTSIVRGIPFWGGSTI<br>DTELKVIDTNCINVIQPDGSYRSEELNLVIIGPSADIIQFECKSFGHEVLNLTRNGYGST<br>QYIRFSPDFTFGFEESLEVDTNPLLGAGKFATDPAVTLAHELIHAGHRLYGIAINPNRVF<br>KVNTNAYYEMSGLEVSFEELRTFGGHDAKFIDSLOENEFRLYYYNKFKDIASTLNKAKSI<br>VGTTASLQYMKNVFKEKYLLSEDTSGKFSVDKLKFDKLYKMLTEIYTEDNFVKFFKVLNR<br>KTYLNFDKAVFKINIVPKVNYTIYDGFNLRNTNLAANFNGQNTEINNMNFTKLKNFTGLF<br>EFYKLLCVRGIITSKAGAGKSLVPRGSAGAGALNDLCIKVNNWDLFFSPSEDNFTNDLNK<br>GEEITSDTNIEAAEENISLDLIQQYYLTFNFDNEPENISIENLSSDIIGOLELMPNIERF<br>PNGKKYELDKYTMFHYLRAQEFEHGKSRIALTNSVNEALLNPSRVYTFFSSDYVKKVNKA<br>TEAAMFLGWVEQLVYDFTDETSEVSTTDKIADITIIIPYIGPALNIGNMLYKDDFVGALI<br>FSGAVILLEFIPEIAIPVLGTFALVSYIANKVLTVQTIDNALSKRNEKWDEVYKYIVTNW<br>LAKVNTQIDLIRKKMKEALENQAEATKAIINYQYNQYTEEEKNNINFNIDDLSSKLNESI<br>NKAMININKFLNQCSVSYLMNSMIPYGVKRLEDFDASLKDALLKYIYDNRGTLIGQVDRL<br>KDKVNNTLSTDIPFQLSKYVDNORLLSTFTEYIKNIINTSILNLRYESNHLIDLSRYASK |

TABLE 1-continued

Sequences

INIGSKVNFDPIDKNQIQLFNLESSKIEVILKNAIVYNSMYENFSTSFWIRIPKYFNSIS
LNNEYTIINCMENNSGWKVSLNYGEIIWTLQDTQEIKORVVFKYSQMINISDYINRWIFV
TITNNRLNNSKIYINGRLIDQKPISNLGNIHASNNIMFKLDGCRDTHRYIWIKYFNLFDK
ELNEKEIKDLYDNQSNSGILKDFWGDYLOYDKPYYMLNLYDPNKYVDVNNVGIRGYMYLK
GPRGSVMTTNIYLNSSLYRGTKFIIKKYASGNKDNIVRNNDRVYINVVVKNKEYRLATNA
SQAGVEKILSALEIPDVGNLSQVVVMKSKNDOGITNKCKMNLQDNNGNDIGFIGFHQFNN
IAKLVASNWYNRQIERSSRTLGCSWEFIPVDDGWGERPLSPAGSPTSTEEGTSESATPES
GPGTSTEPSEGSAPGSPAGSPTSTEEGTSTEPSEGSAPGTSTEPSEGSAPGTSESATPES
GPGSEPATSGSETPGSEPATSGSETPGSPAGSPTSTEEGTSESATPESGPGTSTEPSEGS
APGTSTEPSEGSAPGSPAGSPTSTEEGTSTEPSEGSAPGTSTEPSEGSAPGTSESATPEG
DLVPRGSANSSSVDKLWSHPQFEK

SEQ ID NO 5: (PASTGE100) (nucleic acid sequence)
TCTCCGGCTGGGTCTCCAACATCGACTGAAGAGGGTACGTCTGAGAGTGCTACACCCGAG
AGCGGTCCAGGCACATCCACGGAGCCATCCGAAGGGTCAGCGCCCGGAAGCCCGGCGGGT
TCCCCGACATCGACTGAGGAGGGCACCTCAACAGAACCTAGCGAGGGTAGTGCACCGGGG
ACCAGCACTGAGCCCTCCGAAGGCTCCGCGCCAGGGACAAGTGAGTCCGCAACGCCAGAG
AGCGGCCCAGGCAGCGAGCCTGCCACGAGTGGGTCAGAGACGCCGGGGTCAGAACCTGCG SEQ ID NO 6: (PASTGE200) (nucleic acid sequence)
TCTCCGGCGGGTTCTCCGACCTCTACCGAAGAAGGTACCTCTGAATCTGCGACCCCGGAA
TCTGGTCCGGGTACCTCTACCGAACCGTCTGAAGGTTCTGCGCCGGGTTCTCCGGCGGGT
TCTCCGACCTCTACCGAAGAAGGTACCTCTACCGAACCGTCTGAAGGTTCTGCGCCGGGT
ACCTCTACCGAACCGTCTGAAGGTTCTGCGCCGGGTACCTCTGAATCTGCGACCCCGGAA
TCTGGTCCGGGTTCTGAACCGGCGACCTCTGGTTCTGAAACCCCGGGTTCTGAACCGGCG
ACCTCTGGTTCTGAAACCCCGGGTTCTCCGGCGGGTTCTCCGACCTCTACCGAAGAAGGT
ACCTCTGAATCTGCGACCCCGGAATCTGGTCCGGGTACCTCTACCGAACCGTCTGAAGGT
TCTGCGCCGGGTACCTCTACCGAACCGTCTGAAGGTTCTGCGCCGGGTTCTCCGGCGGGT
TCTCCGACCTCTACCGAAGAAGGTACCTCTACCGAACCGTCTGAAGGTTCTGCGCCGGGT
ACCTCTACCGAACCGTCTGAAGGTTCTGCGCCGGGTACCTCTGAATCTGCGACCCCGGAA

SEQUENCE LISTING

```
<160> NUMBER OF SEQ ID NOS: 6

<210> SEQ ID NO 1
<211> LENGTH: 100
<212> TYPE: PRT
<213> ORGANISM: Artificial Sequence
<220> FEATURE:
<223> OTHER INFORMATION: PASTGE100

<400> SEQUENCE: 1

Ser Pro Ala Gly Ser Pro Thr Ser Thr Glu Glu Gly Thr Ser Glu Ser
1               5                   10                  15

Ala Thr Pro Glu Ser Gly Pro Gly Thr Ser Thr Glu Pro Ser Glu Gly
            20                  25                  30

Ser Ala Pro Gly Ser Pro Ala Gly Ser Pro Thr Ser Thr Glu Glu Gly
        35                  40                  45

Thr Ser Thr Glu Pro Ser Glu Gly Ser Ala Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Glu Pro Ala Thr Ser Gly Ser Glu Thr Pro Gly
                85                  90                  95

Ser Glu Pro Ala
            100


<210> SEQ ID NO 2
<211> LENGTH: 200
<212> TYPE: PRT
<213> ORGANISM: Artificial Sequence
<220> FEATURE:
<223> OTHER INFORMATION: PASTGE200
```

<400> SEQUENCE: 2

Ser Pro Ala Gly Ser Pro Thr Ser Thr Glu Glu Gly Thr Ser Glu Ser
1 5 10 15

Ala Thr Pro Glu Ser Gly Pro Gly Thr Ser Thr Glu Pro Ser Glu Gly
20 25 30

Ser Ala Pro Gly Ser Pro Ala Gly Ser Pro Thr Ser Thr Glu Glu Gly
35 40 45

Thr Ser Thr Glu Pro Ser Glu Gly Ser Ala Pro Gly Thr Ser Thr Glu
50 55 60

Pro Ser Glu Gly Ser Ala Pro Gly Thr Ser Glu Ser Ala Thr Pro Glu
65 70 75 80

Ser Gly Pro Gly Ser Glu Pro Ala Thr Ser Gly Ser Glu Thr Pro Gly
85 90 95

Ser Glu Pro Ala Thr Ser Gly Ser Glu Thr Pro Gly Ser Pro Ala Gly
100 105 110

Ser Pro Thr Ser Thr Glu Glu Gly Thr Ser Glu Ser Ala Thr Pro Glu
115 120 125

Ser Gly Pro Gly Thr Ser Thr Glu Pro Ser Glu Gly Ser Ala Pro Gly
130 135 140

Thr Ser Thr Glu Pro Ser Glu Gly Ser Ala Pro Gly Ser Pro Ala Gly
145 150 155 160

Ser Pro Thr Ser Thr Glu Glu Gly Thr Ser Thr Glu Pro Ser Glu Gly
165 170 175

Ser Ala Pro Gly Thr Ser Thr Glu Pro Ser Glu Gly Ser Ala Pro Gly
180 185 190

Thr Ser Glu Ser Ala Thr Pro Glu
195 200

<210> SEQ ID NO 3
<211> LENGTH: 4935
<212> TYPE: DNA
<213> ORGANISM: Artificial Sequence
<220> FEATURE:
<223> OTHER INFORMATION: PASTGE100-BoNT/A- PASTGE 200

<400> SEQUENCE: 3
atgggtagca gccatcatca tcaccatcat ggtagcctgg ttccgcgtag ctcttctccg 60
gctgggtctc caacatcgac tgaagagggt acgtctgaga gtgctacacc cgagagcggt 120
ccaggcacat ccacggagcc atccgaaggg tcagcgcccg gaagcccggc gggttccccg 180
acatcgactg aggagggcac ctcaacagaa cctagcgagg gtagtgcacc ggggaccagc 240
actgagccct ccgaaggctc cgcgccaggg acaagtgagt ccgcaacgcc agagagcggc 300
ccaggcagcg agcctgccac gagtgggtca gagacgccgg ggtcagaacc tgcgccattt 360
gtgaacaagc agtttaacta taaggacccg gtgaacggtg tggatatcgc gtatatcaaa 420
atcccgaatg cgggccagat gcaaccagtc aaggcgttca agattcataa caagatttgg 480
gttattccgg aacgtgatac cttcaccaat ccggaagaag gcgatttaaa tccgccgcca 540
gaagccaaac aagtgccggt gagctactat gatagcacgt atcttagcac cgataatgaa 600
aaagacaatt acctgaaggg cgtgaccaag ttgttcgagc gcatctacag taccgactta 660
ggccgcatgt tgttgacgag catcgttcgc ggtatcccgt tctggggcgg ctcgaccatt 720
gataccgagt tgaaagtcat tgacacgaac tgtatcaatg ttatccaacc ggacggcagt 780
tatcgcagcg aggagttaaa tttggtcatc atcggtccaa gcgcagatat tattcagttc 840

-continued

```
gaatgcaaga gcttcggcca tgaggtcttg aatttgacgc gcaacggtta cggcagcacc    900
caatacatcc gctttagccc ggatttcacc tttggcttcg aggagagctt ggaggtggac    960
accaacccgc tgttaggtgc cggcaaattc gcaaccgacc cggcagtgac gttggcgcac   1020
gaattgattc atgcgggtca ccgcttatac ggtatcgcga tcaatccgaa tcgcgtcttt   1080
aaagtcaata ccaacgcgta ctacgaaatg agcggcttag aggttagctt tgaagaatta   1140
cgcaccttcg gtggccacga cgccaagttc atcgacagcc tgcaggaaaa tgagttccgc   1200
ttgtactatt acaataaatt caaggacatc gcgagcacct taaataaagc aaagagcatt   1260
gtgggcacca ccgcaagctt gcagtacatg aagaacgtat ttaaggaaaa atatttgttg   1320
tcggaggata ccagcgggaa attcagcgtc gataagctga aattcgacaa attgtataaa   1380
atgctgaccg agatttacac cgaggataac ttcgtcaagt tttttaaggt gttaaatcgt   1440
aagacctatt taaactttga taaagcggtg tttaaaatta atatcgtgcc gaaggtgaat   1500
tacaccatct acgatggttt caatttacgc aacacgaatc tggcggcgaa ttttaatggc   1560
caaaacaccg aaattaacaa catgaacttt acgaagttaa agaatttcac gggcttattc   1620
gaattctaca agttattatg cgtgcgcggc atcattacca gcaaggcagg tgcgggcaag   1680
tccttggttc cgcgtggcag cgccggcgcc ggcgcgctca atgatctgtg tattaaagtc   1740
aataactggg acctgttctt cagcccgagc gaggataact ttaccaacga cttaaacaaa   1800
ggcgaggaga tcacgagcga tacgaacatc gaggcggcgg aggaaaatat tagcctggac   1860
ctcattcagc agtactatct gacgttcaat tttgacaatg agccggagaa catcagcatt   1920
gaaaatctca gcagcgacat catcggtcag ttggaactga tgccgaacat tgaacgcttt   1980
ccgaacggca aaaaatatga actggacaag tataccatgt tccattactt acgcgcacag   2040
gaatttgagc acggcaagag ccgcattgcg ctgaccaata gcgttaacga ggccttgtta   2100
aatccgagcc gtgtctacac gttcttcagc agcgattatg tcaaaaaagt gaacaaggcg   2160
accgaagccg cgatgttttt gggctgggtc gagcaattgg tttacgattt taccgacgaa   2220
accagcgagg tgagcacgac cgacaaaatt gcagatatca ccatcatcat tccgtacatc   2280
ggtccggcgc tcaatatcgg caatatgtta tacaaggacg actttgtggg cgcgctgatc   2340
tttagcggcg cggttatctt attagaattc atcccggaga tcgcaatccc ggtcttgggc   2400
acctttgcgt tggtgagcta tatcgcgaat aaagtgctca cggtccaaac catcgataac   2460
gcgctcagca agcgtaatga gaaatgggac gaggtttata agtatatcgt gaccaactgg   2520
ttagcaaaag tcaatacgca gatcgatctc atccgcaaaa aaatgaaaga agccttggaa   2580
aatcaagcgg aggcaaccaa agccatcatt aattaccagt ataaccaata taccgaagaa   2640
gaaaaaaaca atatcaactt caatatcgat gatttgagca gcaaactgaa cgagagcatt   2700
aacaaagcga tgattaacat caacaagttc ttgaatcaat gcagcgtgag ctatctcatg   2760
aacagcatga tcccgtatgg cgtcaaacgc ttggaagatt ttgacgccag cctgaaagat   2820
gcgctcctca agtatattta tgacaaccgc ggcaccctca ttggccaggt ggaccgcttg   2880
aaggataaag tgaacaatac gctcagcacg gatatcccgt tccagctgag caagtacgtc   2940
gacaaccagc gcttactgag cacctttacc gagtatatca agaacatcat taataccagc   3000
atcctcaact tgcgctatga gagcaatcac ctgatcgacc tcagccgcta cgccagcaag   3060
atcaacatcg gcagcaaggt caatttcgac ccgatcgata agaatcagat ccaattgttt   3120
aacctggaaa gcagcaagat cgaggttatc ttgaagaacg cgattgtgta caacagcatg   3180
tacgagaact ttagcacgag cttctggatt cgtatcccga agtatttcaa tagcattagc   3240
```

-continued ctgaataacg aatataccat tatcaactgc atggaaaata atagcggctg gaaggtgagc 3300
ttaaattacg gcgagatcat ttggacctta caggataccc aagaaatcaa acagcgcgtc 3360
gtctttaagt atagccagat gatcaacatc agcgattaca tcaaccgctg gatcttcgtg 3420
accatcacca ataatcgctt gaataatagc aagatttaca tcaatggtcg cttgattgat 3480
caaaaaccga tcagcaatct cggtaatatc catgccagca ataacatcat gtttaagtta 3540
gacggttgcc gcgataccca ccgctatatc tggatcaagt attttaactt atttgataag 3600
gaactcaacg aaaaggaaat taaagactta tatgacaatc agagcaatag cggcatcctg 3660
aaggatttct ggggcgacta cctgcagtac gataagccgt actatatgtt gaacttgtat 3720
gacccgaaca aatatgtcga tgtgaacaat gtgggtattc gtggctatat gtacttaaag 3780
ggcccgcgtg gtagcgtgat gaccacgaat atttacttaa acagcagctt ataccgcggc 3840
acgaagttta ttatcaagaa gtatgccagc ggcaacaagg acaatatcgt ccgcaacaac 3900
gaccgtgtgt atattaacgt ggtggtgaag aataaagagt accgcttggc cacgaatgcg 3960
agccaggcgg gcgtggaaaa aatcttgagc gcgttggaga tcccggacgt cggcaacctc 4020
agccaggttg tggtgatgaa gtctaaaaac gaccagggca tcacgaacaa gtgcaaaatg 4080
aatttgcaag ataacaacgg caacgacatc ggctttattg gttttcacca gttcaataac 4140
atcgccaaac tcgtggccag caattggtat aaccgccaaa ttgaacgcag cagccgcacg 4200
ctcggctgta gctgggagtt catcccggtg gacgatggct ggggcgagcg cccgctctct 4260
ccggcgggtt ctccgacctc taccgaagaa ggtacctctg aatctgcgac cccggaatct 4320
ggtccgggta cctctaccga accgtctgaa ggttctgcgc cgggttctcc ggcgggttct 4380
ccgacctcta ccgaagaagg tacctctacc gaaccgtctg aaggttctgc gccgggtacc 4440
tctaccgaac cgtctgaagg ttctgcgccg ggtacctctg aatctgcgac cccggaatct 4500
ggtccgggtt ctgaaccggc gacctctggt tctgaaaccc cgggttctga accggcgacc 4560
tctggttctg aaaccccggg ttctccggcg ggttctccga cctctaccga agaaggtacc 4620
tctgaatctg cgaccccgga atctggtccg ggtacctcta ccgaaccgtc tgaaggttct 4680
gcgccgggta cctctaccga accgtctgaa ggttctgcgc cgggttctcc ggcgggttct 4740
ccgacctcta ccgaagaagg tacctctacc gaaccgtctg aaggttctgc gccgggtacc 4800
tctaccgaac cgtctgaagg ttctgcgccg ggtacctctg aatctgcgac cccggaagga 4860
gatctggtgc cacgcggttc cgcgaattcg agctccgtcg acaagctttg gagccacccg 4920
cagttcgaaa aataa 4935

<210> SEQ ID NO 4
<211> LENGTH: 1644
<212> TYPE: PRT
<213> ORGANISM: Artificial Sequence
<220> FEATURE:
<223> OTHER INFORMATION: PASTGE100-BoNT/A- PASTGE 200

<400> SEQUENCE: 4

Met Gly Ser Ser His His His His His His Gly Ser Leu Val Pro Arg
1               5                   10                  15

Ser Ser Ser Pro Ala Gly Ser Pro Thr Ser Thr Glu Glu Gly Thr Ser
            20                  25                  30

Glu Ser Ala Thr Pro Glu Ser Gly Pro Gly Thr Ser Thr Glu Pro Ser
        35                  40                  45

Glu Gly Ser Ala Pro Gly Ser Pro Ala Gly Ser Pro Thr Ser Thr Glu

-continued

```
    50                  55                  60

Glu Gly Thr Ser Thr Glu Pro Ser Glu Gly Ser Ala Pro Gly Thr Ser
65                  70                  75                  80

Thr Glu Pro Ser Glu Gly Ser Ala Pro Gly Thr Ser Glu Ser Ala Thr
                85                  90                  95

Pro Glu Ser Gly Pro Gly Ser Glu Pro Ala Thr Ser Gly Ser Glu Thr
            100                 105                 110

Pro Gly Ser Glu Pro Ala Pro Phe Val Asn Lys Gln Phe Asn Tyr Lys
        115                 120                 125

Asp Pro Val Asn Gly Val Asp Ile Ala Tyr Ile Lys Ile Pro Asn Ala
    130                 135                 140

Gly Gln Met Gln Pro Val Lys Ala Phe Lys Ile His Asn Lys Ile Trp
145                 150                 155                 160

Val Ile Pro Glu Arg Asp Thr Phe Thr Asn Pro Glu Glu Gly Asp Leu
                165                 170                 175

Asn Pro Pro Pro Glu Ala Lys Gln Val Pro Val Ser Tyr Tyr Asp Ser
            180                 185                 190

Thr Tyr Leu Ser Thr Asp Asn Glu Lys Asp Asn Tyr Leu Lys Gly Val
        195                 200                 205

Thr Lys Leu Phe Glu Arg Ile Tyr Ser Thr Asp Leu Gly Arg Met Leu
    210                 215                 220

Leu Thr Ser Ile Val Arg Gly Ile Pro Phe Trp Gly Gly Ser Thr Ile
225                 230                 235                 240

Asp Thr Glu Leu Lys Val Ile Asp Thr Asn Cys Ile Asn Val Ile Gln
                245                 250                 255

Pro Asp Gly Ser Tyr Arg Ser Glu Glu Leu Asn Leu Val Ile Ile Gly
            260                 265                 270

Pro Ser Ala Asp Ile Ile Gln Phe Glu Cys Lys Ser Phe Gly His Glu
        275                 280                 285

Val Leu Asn Leu Thr Arg Asn Gly Tyr Gly Ser Thr Gln Tyr Ile Arg
    290                 295                 300

Phe Ser Pro Asp Phe Thr Phe Gly Phe Glu Glu Ser Leu Glu Val Asp
305                 310                 315                 320

Thr Asn Pro Leu Leu Gly Ala Gly Lys Phe Ala Thr Asp Pro Ala Val
                325                 330                 335

Thr Leu Ala His Glu Leu Ile His Ala Gly His Arg Leu Tyr Gly Ile
            340                 345                 350

Ala Ile Asn Pro Asn Arg Val Phe Lys Val Asn Thr Asn Ala Tyr Tyr
        355                 360                 365

Glu Met Ser Gly Leu Glu Val Ser Phe Glu Glu Leu Arg Thr Phe Gly
    370                 375                 380

Gly His Asp Ala Lys Phe Ile Asp Ser Leu Gln Glu Asn Glu Phe Arg
385                 390                 395                 400

Leu Tyr Tyr Tyr Asn Lys Phe Lys Asp Ile Ala Ser Thr Leu Asn Lys
                405                 410                 415

Ala Lys Ser Ile Val Gly Thr Thr Ala Ser Leu Gln Tyr Met Lys Asn
            420                 425                 430

Val Phe Lys Glu Lys Tyr Leu Leu Ser Glu Asp Thr Ser Gly Lys Phe
        435                 440                 445

Ser Val Asp Lys Leu Lys Phe Asp Lys Leu Tyr Lys Met Leu Thr Glu
    450                 455                 460

Ile Tyr Thr Glu Asp Asn Phe Val Lys Phe Phe Lys Val Leu Asn Arg
465                 470                 475                 480
```

-continued

```
Lys Thr Tyr Leu Asn Phe Asp Lys Ala Val Phe Lys Ile Asn Ile Val
                485                 490                 495

Pro Lys Val Asn Tyr Thr Ile Tyr Asp Gly Phe Asn Leu Arg Asn Thr
            500                 505                 510

Asn Leu Ala Ala Asn Phe Asn Gly Gln Asn Thr Glu Ile Asn Asn Met
        515                 520                 525

Asn Phe Thr Lys Leu Lys Asn Phe Thr Gly Leu Phe Glu Phe Tyr Lys
    530                 535                 540

Leu Leu Cys Val Arg Gly Ile Ile Thr Ser Lys Ala Gly Ala Gly Lys
545                 550                 555                 560

Ser Leu Val Pro Arg Gly Ser Ala Gly Ala Gly Ala Leu Asn Asp Leu
                565                 570                 575

Cys Ile Lys Val Asn Asn Trp Asp Leu Phe Phe Ser Pro Ser Glu Asp
            580                 585                 590

Asn Phe Thr Asn Asp Leu Asn Lys Gly Glu Glu Ile Thr Ser Asp Thr
        595                 600                 605

Asn Ile Glu Ala Ala Glu Glu Asn Ile Ser Leu Asp Leu Ile Gln Gln
    610                 615                 620

Tyr Tyr Leu Thr Phe Asn Phe Asp Asn Glu Pro Glu Asn Ile Ser Ile
625                 630                 635                 640

Glu Asn Leu Ser Ser Asp Ile Ile Gly Gln Leu Glu Leu Met Pro Asn
                645                 650                 655

Ile Glu Arg Phe Pro Asn Gly Lys Lys Tyr Glu Leu Asp Lys Tyr Thr
            660                 665                 670

Met Phe His Tyr Leu Arg Ala Gln Glu Phe Glu His Gly Lys Ser Arg
        675                 680                 685

Ile Ala Leu Thr Asn Ser Val Asn Glu Ala Leu Leu Asn Pro Ser Arg
    690                 695                 700

Val Tyr Thr Phe Phe Ser Ser Asp Tyr Val Lys Lys Val Asn Lys Ala
705                 710                 715                 720

Thr Glu Ala Ala Met Phe Leu Gly Trp Val Glu Gln Leu Val Tyr Asp
                725                 730                 735

Phe Thr Asp Glu Thr Ser Glu Val Ser Thr Thr Asp Lys Ile Ala Asp
            740                 745                 750

Ile Thr Ile Ile Ile Pro Tyr Ile Gly Pro Ala Leu Asn Ile Gly Asn
        755                 760                 765

Met Leu Tyr Lys Asp Asp Phe Val Gly Ala Leu Ile Phe Ser Gly Ala
    770                 775                 780

Val Ile Leu Leu Glu Phe Ile Pro Glu Ile Ala Ile Pro Val Leu Gly
785                 790                 795                 800

Thr Phe Ala Leu Val Ser Tyr Ile Ala Asn Lys Val Leu Thr Val Gln
                805                 810                 815

Thr Ile Asp Asn Ala Leu Ser Lys Arg Asn Glu Lys Trp Asp Glu Val
            820                 825                 830

Tyr Lys Tyr Ile Val Thr Asn Trp Leu Ala Lys Val Asn Thr Gln Ile
        835                 840                 845

Asp Leu Ile Arg Lys Lys Met Lys Glu Ala Leu Glu Asn Gln Ala Glu
    850                 855                 860

Ala Thr Lys Ala Ile Ile Asn Tyr Gln Tyr Asn Gln Tyr Thr Glu Glu
865                 870                 875                 880

Glu Lys Asn Asn Ile Asn Phe Asn Ile Asp Asp Leu Ser Ser Lys Leu
                885                 890                 895
```

-continued

```
Asn Glu Ser Ile Asn Lys Ala Met Ile Asn Ile Asn Lys Phe Leu Asn
            900                 905                 910

Gln Cys Ser Val Ser Tyr Leu Met Asn Ser Met Ile Pro Tyr Gly Val
        915                 920                 925

Lys Arg Leu Glu Asp Phe Asp Ala Ser Leu Lys Asp Ala Leu Leu Lys
    930                 935                 940

Tyr Ile Tyr Asp Asn Arg Gly Thr Leu Ile Gly Gln Val Asp Arg Leu
945                 950                 955                 960

Lys Asp Lys Val Asn Asn Thr Leu Ser Thr Asp Ile Pro Phe Gln Leu
                965                 970                 975

Ser Lys Tyr Val Asp Asn Gln Arg Leu Leu Ser Thr Phe Thr Glu Tyr
            980                 985                 990

Ile Lys Asn Ile Ile Asn Thr Ser Ile Leu Asn Leu Arg Tyr Glu Ser
        995                 1000                1005

Asn His Leu Ile Asp Leu Ser Arg Tyr Ala Ser Lys Ile Asn Ile Gly
    1010                1015                1020

Ser Lys Val Asn Phe Asp Pro Ile Asp Lys Asn Gln Ile Gln Leu Phe
1025                1030                1035                1040

Asn Leu Glu Ser Ser Lys Ile Glu Val Ile Leu Lys Asn Ala Ile Val
                1045                1050                1055

Tyr Asn Ser Met Tyr Glu Asn Phe Ser Thr Ser Phe Trp Ile Arg Ile
            1060                1065                1070

Pro Lys Tyr Phe Asn Ser Ile Ser Leu Asn Asn Glu Tyr Thr Ile Ile
        1075                1080                1085

Asn Cys Met Glu Asn Asn Ser Gly Trp Lys Val Ser Leu Asn Tyr Gly
    1090                1095                1100

Glu Ile Ile Trp Thr Leu Gln Asp Thr Gln Glu Ile Lys Gln Arg Val
1105                1110                1115                1120

Val Phe Lys Tyr Ser Gln Met Ile Asn Ile Ser Asp Tyr Ile Asn Arg
                1125                1130                1135

Trp Ile Phe Val Thr Ile Thr Asn Asn Arg Leu Asn Asn Ser Lys Ile
            1140                1145                1150

Tyr Ile Asn Gly Arg Leu Ile Asp Gln Lys Pro Ile Ser Asn Leu Gly
        1155                1160                1165

Asn Ile His Ala Ser Asn Asn Ile Met Phe Lys Leu Asp Gly Cys Arg
    1170                1175                1180

Asp Thr His Arg Tyr Ile Trp Ile Lys Tyr Phe Asn Leu Phe Asp Lys
1185                1190                1195                1200

Glu Leu Asn Glu Lys Glu Ile Lys Asp Leu Tyr Asp Asn Gln Ser Asn
                1205                1210                1215

Ser Gly Ile Leu Lys Asp Phe Trp Gly Asp Tyr Leu Gln Tyr Asp Lys
            1220                1225                1230

Pro Tyr Tyr Met Leu Asn Leu Tyr Asp Pro Asn Lys Tyr Val Asp Val
        1235                1240                1245

Asn Asn Val Gly Ile Arg Gly Tyr Met Tyr Leu Lys Gly Pro Arg Gly
    1250                1255                1260

Ser Val Met Thr Thr Asn Ile Tyr Leu Asn Ser Ser Leu Tyr Arg Gly
1265                1270                1275                1280

Thr Lys Phe Ile Ile Lys Lys Tyr Ala Ser Gly Asn Lys Asp Asn Ile
                1285                1290                1295

Val Arg Asn Asn Asp Arg Val Tyr Ile Asn Val Val Val Lys Asn Lys
            1300                1305                1310

Glu Tyr Arg Leu Ala Thr Asn Ala Ser Gln Ala Gly Val Glu Lys Ile
```

-continued

```
        1315                1320                1325

Leu Ser Ala Leu Glu Ile Pro Asp Val Gly Asn Leu Ser Gln Val Val
    1330                1335                1340

Val Met Lys Ser Lys Asn Asp Gln Gly Ile Thr Asn Lys Cys Lys Met
1345                1350                1355                1360

Asn Leu Gln Asp Asn Asn Gly Asn Asp Ile Gly Phe Ile Gly Phe His
                1365                1370                1375

Gln Phe Asn Asn Ile Ala Lys Leu Val Ala Ser Asn Trp Tyr Asn Arg
            1380                1385                1390

Gln Ile Glu Arg Ser Ser Arg Thr Leu Gly Cys Ser Trp Glu Phe Ile
        1395                1400                1405

Pro Val Asp Asp Gly Trp Gly Glu Arg Pro Leu Ser Pro Ala Gly Ser
    1410                1415                1420

Pro Thr Ser Thr Glu Glu Gly Thr Ser Glu Ser Ala Thr Pro Glu Ser
1425                1430                1435                1440

Gly Pro Gly Thr Ser Thr Glu Pro Ser Glu Gly Ser Ala Pro Gly Ser
                1445                1450                1455

Pro Ala Gly Ser Pro Thr Ser Thr Glu Glu Gly Thr Ser Thr Glu Pro
            1460                1465                1470

Ser Glu Gly Ser Ala Pro Gly Thr Ser Thr Glu Pro Ser Glu Gly Ser
        1475                1480                1485

Ala Pro Gly Thr Ser Glu Ser Ala Thr Pro Glu Ser Gly Pro Gly Ser
    1490                1495                1500

Glu Pro Ala Thr Ser Gly Ser Glu Thr Pro Gly Ser Glu Pro Ala Thr
1505                1510                1515                1520

Ser Gly Ser Glu Thr Pro Gly Ser Pro Ala Gly Ser Pro Thr Ser Thr
                1525                1530                1535

Glu Glu Gly Thr Ser Glu Ser Ala Thr Pro Glu Ser Gly Pro Gly Thr
            1540                1545                1550

Ser Thr Glu Pro Ser Glu Gly Ser Ala Pro Gly Thr Ser Thr Glu Pro
        1555                1560                1565

Ser Glu Gly Ser Ala Pro Gly Ser Pro Ala Gly Ser Pro Thr Ser Thr
    1570                1575                1580

Glu Glu Gly Thr Ser Thr Glu Pro Ser Glu Gly Ser Ala Pro Gly Thr
1585                1590                1595                1600

Ser Thr Glu Pro Ser Glu Gly Ser Ala Pro Gly Thr Ser Glu Ser Ala
                1605                1610                1615

Thr Pro Glu Gly Asp Leu Val Pro Arg Gly Ser Ala Asn Ser Ser Ser
            1620                1625                1630

Val Asp Lys Leu Trp Ser His Pro Gln Phe Glu Lys
        1635                1640


<210> SEQ ID NO 5
<211> LENGTH: 300
<212> TYPE: DNA
<213> ORGANISM: Artificial Sequence
<220> FEATURE:
<223> OTHER INFORMATION: PASTGE100

<400> SEQUENCE: 5

tctccggctg ggtctccaac atcgactgaa gagggtacgt ctgagagtgc tacacccgag     60

agcggtccag gcacatccac ggagccatcc gaagggtcag cgcccggaag cccggcgggt    120

tccccgacat cgactgagga gggcacctca acagaaccta gcgagggtag tgcaccgggg    180

accagcactg agccctccga aggctccgcg ccagggacaa gtgagtccgc aacgccagag    240
```

-continued

```
agcggcccag gcagcgagcc tgccacgagt gggtcagaga cgccggggtc agaacctgcg    300


<210> SEQ ID NO 6
<211> LENGTH: 600
<212> TYPE: DNA
<213> ORGANISM: Artificial Sequence
<220> FEATURE:
<223> OTHER INFORMATION: PASTGE200

<400> SEQUENCE: 6

tctccggcgg gttctccgac ctctaccgaa gaaggtacct ctgaatctgc gaccccggaa     60

tctggtccgg gtacctctac cgaaccgtct gaaggttctg cgccgggttc tccggcgggt    120

tctccgacct ctaccgaaga aggtacctct accgaaccgt ctgaaggttc tgcgccgggt    180

acctctaccg aaccgtctga aggttctgcg ccgggtacct ctgaatctgc gaccccggaa    240

tctggtccgg gttctgaacc ggcgacctct ggttctgaaa ccccgggttc tgaaccggcg    300

acctctggtt ctgaaacccc gggttctccg gcgggttctc cgacctctac cgaagaaggt    360

acctctgaat ctgcgacccc ggaatctggt ccgggtacct ctaccgaacc gtctgaaggt    420

tctgcgccgg gtacctctac cgaaccgtct gaaggttctg cgccgggttc tccggcgggt    480

tctccgacct ctaccgaaga aggtacctct accgaaccgt ctgaaggttc tgcgccgggt    540

acctctaccg aaccgtctga aggttctgcg ccgggtacct ctgaatctgc gaccccggaa    600
```

The invention claimed is:

1. A recombinant botulinum neurotoxin comprising: a functionally active botulinum neurotoxin light chain, a functionally active botulinum neurotoxin heavy chain, and at least one domain, wherein the botulinum neurotoxin is selected from *Clostridium botulinum* neurotoxin serotype A, E, and C; wherein said at least one domain consists of 100-500 amino acid residues consisting of a plurality of amino acid repeats consisting of proline, alanine, serine, threonine, glycine and glutamate residues, wherein no more than six consecutive amino acid residues are identical, and wherein said at least one domain comprises the amino acid sequence of SEQ ID NO: 1, wherein said at least one domain is inserted at a position selected from (i) the N-terminus of the functionally active botulinum neurotoxin light chain, (ii) the C-terminus of the functionally active botulinum neurotoxin light chain, (iii) the N-terminus of the functionally active botulinum neurotoxin heavy chain, or (iv) the C-terminus of the functionally active botulinum neurotoxin heavy chain, and wherein the recombinant botulinum neurotoxin exhibits an increased duration of effect without a delayed onset of effect relative to a wild type botulinum neurotoxin without said at least one domain.

2. The recombinant botulinum neurotoxin of claim 1, wherein the botulinum neurotoxin is selected from *Clostridium botulinum* neurotoxin serotype A.

3. The recombinant botulinum neurotoxin of claim 1, wherein said at least one domain comprises the following amino acid sequence:

```
                                                   (SEQ ID NO: 2)
SPAGSPTSTEEGTSESATPESGPGTSTEPSEGSAPGSPAGSPTSTEEG

TSTEPSEGSAPGTSTEPSEGSAPGTSESATPESGPGSEPATSGSETPG

SEPATSGSETPGSPAGSPTSTEEGTSESATPESGPGTSTEPSEGSAPG
```

-continued

```
TSTEPSEGSAPGSPAGSPTSTEEGTSTEPSEGSAPGTSTEPSEGSAPG

TSESATPE.
```

4. The recombinant botulinum neurotoxin of claim 1, wherein the botulinum neurotoxin comprises at least one domain comprising the amino acid sequence of SEQ ID NO: 1 and one domain comprising the amino acid sequence of SEQ ID NO: 2.

5. The recombinant botulinum neurotoxin of claim 4, wherein (i) the domain comprising the amino acid sequence of SEQ ID NO: 1 is inserted at a position of the N-terminus of the functionally active botulinum neurotoxin light chain, and (ii) the domain comprising the amino acid sequence of SEQ ID NO: 2 is inserted at a position of the C-terminus of the functionally active botulinum neurotoxin heavy chain.

6. A composition comprising the recombinant botulinum neurotoxin of claim 1 and a solvent or excipient.

7. A pharmaceutical composition comprising the recombinant botulinum neurotoxin of claim 1 and one or more pharmaceutically acceptable carriers.

8. A method of using a recombinant botulinum neurotoxin for cosmetic treatment, said method comprising the step of administering the recombinant botulinum neurotoxin of claim 1 to a patient.

9. A method for the generation of a recombinant botulinum neurotoxin according to claim 1, comprising the step of obtaining a recombinant nucleic acid sequence encoding a recombinant single-chain precursor botulinum neurotoxin by the insertion of a nucleic acid sequence encoding said domain into a nucleic acid sequence encoding a parental botulinum neurotoxin, wherein said method further comprises the step of heterologously expressing said recombinant botulinum neurotoxin in a host cell from said nucleic acid sequence.

10. A recombinant single-chain botulinum neurotoxin, which is a precursor comprising the recombinant botulinum neurotoxin of claim 1.

11. A nucleic acid sequence encoding the recombinant single-chain botulinum neurotoxin of claim 10.

12. The nucleic acid sequence of claim 11, wherein the nucleic acid sequence has the nucleotide sequence of SEQ ID NO: 3.

13. The recombinant botulinum neurotoxin of claim 1, wherein said at least one domain consists of between 100 and 300 amino acid residues.

14. The method of claim 9, wherein the host cell is a bacterial host cell.

15. The method of claim 9, wherein the host cell is an *E. coli* host cell.

16. The recombinant botulinum neurotoxin of claim 1, wherein the botulinum neurotoxin comprises a first domain inserted at a position of the N-terminus of the functionally active botulinum neurotoxin light chain, and a second domain inserted at a position of the C-terminus of the functionally active botulinum neurotoxin heavy chain, wherein both the first and second domain consist of 100-500 amino acid residues consisting of a plurality of amino acid repeats consisting of proline, alanine, serine, threonine, glycine and glutamate residues, wherein no more than six consecutive amino acid residues are identical, and wherein the first and second domain comprise the amino acid sequence of SEQ ID NO: 1.

* * * * *